US011514553B2

(12) United States Patent
Ootsuki

(10) Patent No.: US 11,514,553 B2
(45) Date of Patent: Nov. 29, 2022

(54) IMAGE PROCESSING DEVICE, IMAGE PROCESSING METHOD, AND INTRAOCULAR IMAGE PROCESSING SYSTEM

(71) Applicant: SONY CORPORATION, Tokyo (JP)

(72) Inventor: Tomoyuki Ootsuki, Tokyo (JP)

(73) Assignee: SONY CORPORATION, Tokyo (JP)

( * ) Notice: Subject to any disclaimer, the term of this patent is extended or adjusted under 35 U.S.C. 154(b) by 58 days.

(21) Appl. No.: 17/057,866

(22) PCT Filed: Mar. 28, 2019

(86) PCT No.: PCT/JP2019/013520
§ 371 (c)(1),
(2) Date: Nov. 23, 2020

(87) PCT Pub. No.: WO2019/230173
PCT Pub. Date: Dec. 5, 2019

(65) Prior Publication Data
US 2021/0209724 A1  Jul. 8, 2021

(30) Foreign Application Priority Data
May 30, 2018 (JP) .............................. JP2018-102938

(51) Int. Cl.
*G06T 3/00* (2006.01)
*A61B 90/20* (2016.01)
*A61B 3/12* (2006.01)

(52) U.S. Cl.
CPC .............. *G06T 3/0031* (2013.01); *A61B 3/12* (2013.01); *A61B 90/20* (2016.02); *G06T 3/0056* (2013.01); *G06T 2210/41* (2013.01)

(58) Field of Classification Search
CPC . G06T 3/0031; G06T 3/0056; G06T 2210/41; A61B 90/20; A61B 3/12;
(Continued)

(56) References Cited

U.S. PATENT DOCUMENTS

2012/0083667 A1    4/2012  Isogai et al.
2013/0188133 A1*   7/2013  Iwase .................. A61B 3/0058
                                              356/479
(Continued)

FOREIGN PATENT DOCUMENTS

BR   102014012709 A2   1/2015
CA         2989094 A1   2/2017
(Continued)

OTHER PUBLICATIONS

International Search Report and Written Opinion of PCT Application No. PCT/JP2019/013520, dated Jun. 18, 2019, 09 pages of ISRWO.

(Continued)

*Primary Examiner* — Chong Wu
(74) *Attorney, Agent, or Firm* — Chip Law Group

(57) ABSTRACT

There is provided an image processing device for observing an inside of an eye in a wider range. The image processing device includes an integration processing unit that integrates ophthalmologic images acquired by a plurality of types of ophthalmologic image capturing devices by correlating intraocular positions and generates one integrated image indicating intraocular information in a range wider than a range indicated by each of the ophthalmologic images.

16 Claims, 23 Drawing Sheets

(58) Field of Classification Search
CPC ....... A61B 3/0025; A61B 3/0058; A61B 3/10; A61B 3/14; G02B 21/0012
See application file for complete search history.

(56) References Cited

U.S. PATENT DOCUMENTS

| | | |
|---|---|---|
| 2014/0347627 A1 | 11/2014 | Imamura |
| 2015/0077528 A1 | 3/2015 | Awdeh |
| 2015/0327762 A1 | 11/2015 | Isogai et al. |
| 2017/0035287 A1 | 2/2017 | Ren et al. |
| 2019/0038364 A1 | 2/2019 | Enoki |

FOREIGN PATENT DOCUMENTS

| | | |
|---|---|---|
| CN | 104173023 A | 12/2014 |
| CN | 107847349 A | 3/2018 |
| CN | 108601670 A | 9/2018 |
| DE | 102013210728 A1 | 12/2014 |
| EP | 2807974 A1 | 12/2014 |
| EP | 3046518 A1 | 7/2016 |
| EP | 3437593 A1 | 2/2019 |
| JP | 2005-304633 A | 11/2005 |
| JP | 4095044 B2 | 6/2008 |
| JP | 2009-183332 A | 8/2009 |
| JP | 5192250 B2 | 5/2013 |
| JP | 5762712 B2 | 8/2015 |
| JP | 6174908 B2 | 8/2017 |
| JP | 2018-068707 A | 5/2018 |
| JP | 2018-528800 A | 10/2018 |
| KR | 10-2014-0139438 A | 12/2014 |
| PH | 12014000147 A1 | 12/2015 |
| RU | 2014121221 A | 12/2015 |
| TW | 201706890 A | 2/2017 |
| WO | 2015/042120 A1 | 3/2015 |
| WO | 2017/021790 A1 | 2/2017 |
| WO | 2017/169283 A1 | 10/2017 |
| WO | 2017/169823 A1 | 10/2017 |

OTHER PUBLICATIONS

Extended European Search Report of EP Application No. 19810390.5 dated Jun. 15, 2021, 05 pages.

* cited by examiner

IMAGE PROCESSING DEVICE, IMAGE PROCESSING METHOD, AND INTRAOCULAR IMAGE PROCESSING SYSTEM

CROSS REFERENCE TO RELATED APPLICATIONS

This application is a U.S. National Phase of International Patent Application No. PCT/JP2019/013520 filed on Mar. 28, 2019, which claims priority benefit of Japanese Patent Application No. JP 2018-102938 filed in the Japan Patent Office on May 30, 2018. Each of the above-referenced applications is hereby incorporated herein by reference in its entirety.

TECHNICAL FIELD

The present disclosure relates to an image processing device, an image processing method, and an intraocular image processing system.

BACKGROUND ART

In retinal surgical operations, while there is a demand for always observing a wide range simultaneously in order to determine retinal traction by the vitreous body and the like, for example, there is a demand for enlarging and observing the posterior pole when providing treatment for the posterior pole. For example, for posterior pole observation of observing the posterior pole of an eyeball, a contact lens to be mounted on the eyeball, a non-contact lens, or the like is used. Meanwhile, for wide-angle observation of observing the fundus of the eyeball in a wide range, a wide-angle observation lens and the like is used. The wide-angle observation lens is provided in a surgical microscope as an additional optical system, for example, in a wide-angle observation system for observing a real image created by the additional optical system. The observation range for wide-angle observation is wider than the observation range for posterior pole observation.

CITATION LIST

Patent Document

Patent Document 1: WO 2017/169283

SUMMARY OF THE INVENTION

Problems to be Solved by the Invention

The use of the surgical microscope and the wide-angle observation system makes it possible to observe the inside of the eye in a wide range simultaneously, but the range of the observation is limited. Therefore, in a case where it is desired to observe the inside of the eye in a wider range, in addition to images acquired by the surgical microscope, it is also considered, for example, to present an image acquired by an image generating device including an intraocular endoscope and the like. At this time, by showing which position in the eye each image indicates, it is possible to easily determine the position and direction of a surgical operation member. For example, Patent Document 1 discloses a technique for displaying an image representing a relative posture of an intraocular endoscope in the eye, and an intraocular endoscopic image captured by the intraocular endoscope.

With the technique described in Patent Document 1, it is possible to determine which part of the eye is captured to create the intraocular endoscopic image. However, the technique of Patent Document 1 presents an image representing the posture of the intraocular endoscope and the intraocular endoscopic image as separate images or in superimposition, and does not present a wider range of intraocular image than the intraocular endoscopic image.

Therefore, the present disclosure proposes a novel and improved image processing device, an image processing method, and an intraocular image processing system that enable observation of the inside of the eye in a wider range and simultaneously.

Solutions to Problems

According to the present disclosure, there is provided an image processing device including an integration processing unit configured to integrate ophthalmologic images acquired by a plurality of types of ophthalmologic observation devices by correlating intraocular positions and to generate one integrated image indicating intraocular information in a range wider than a range indicated by each of the ophthalmologic images.

Furthermore, according to the present disclosure, there is provided an image processing method including: integrating ophthalmologic images acquired by a plurality of types of ophthalmologic observation devices by correlating intraocular positions; and generating one integrated image indicating intraocular information in a range wider than a range indicated by each of the ophthalmologic images.

Moreover, according to the present disclosure, there is provided an intraocular image processing system including: a plurality of ophthalmologic observation devices configured to acquire ophthalmologic images during an ophthalmologic surgical operation; and an image processing device configured to integrate a plurality of types of the ophthalmologic images acquired by the ophthalmologic observation devices by correlating intraocular positions and to generate one integrated image indicating intraocular information in a range wider than a range indicated by each of the ophthalmologic images.

Effects of the Invention

As described above, the present disclosure enables observation of the inside of the eye in a wider range and simultaneously. Note that above effects are not necessarily restrictive, and in addition to or instead of the effects described above, any of the effects indicated in the present specification or other effects that can be determined from the present specification may be produced.

MODE FOR CARRYING OUT THE INVENTION

Figure 1:
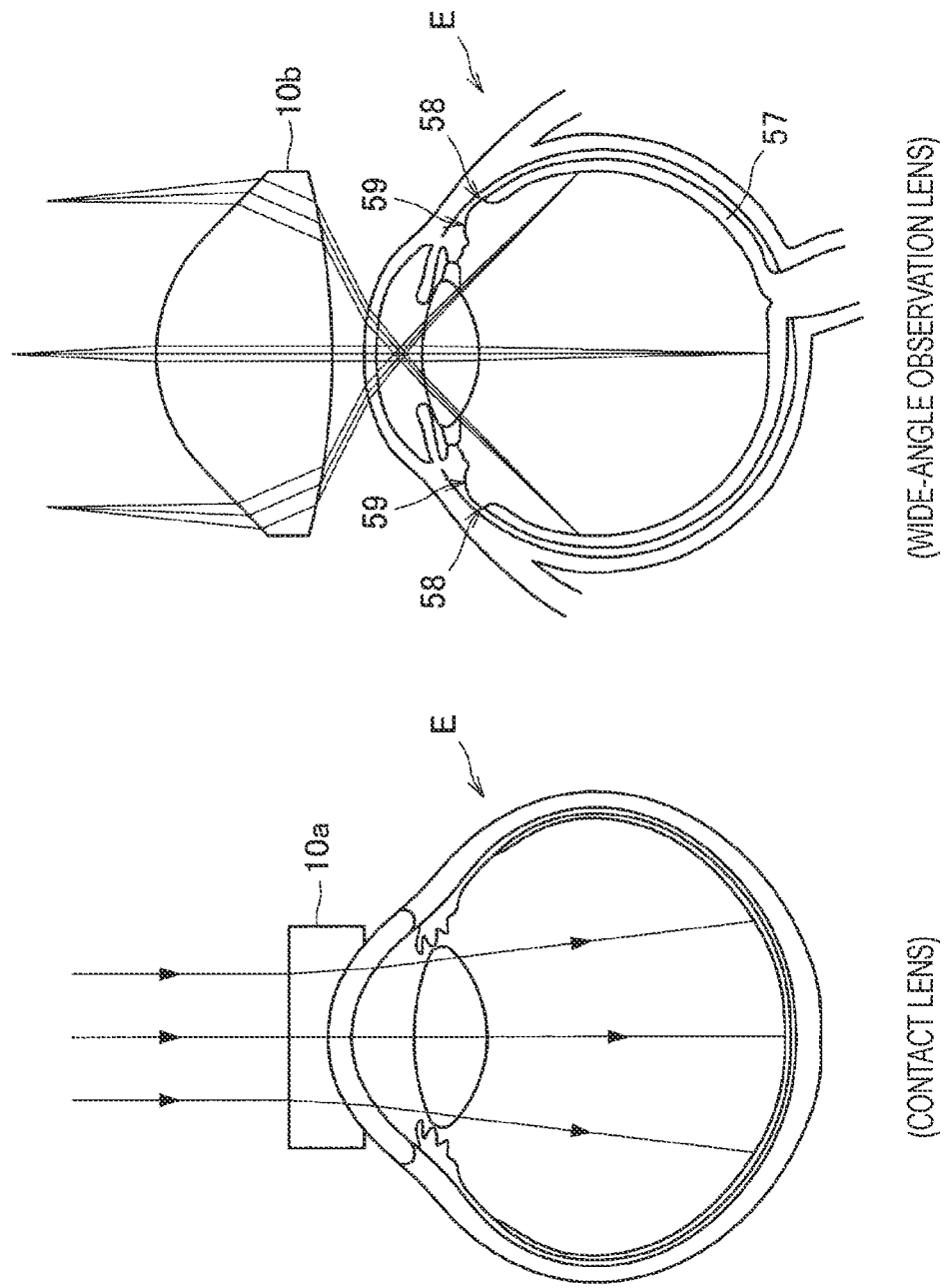
FIG. 1 is an explanatory diagram showing an example of intraocular observation lenses to be used in posterior pole observation and wide-angle observation.

A preferred embodiment of the present disclosure will be described in detail below with reference to the accompanying drawings. Note that in the present specification and the drawings, components having substantially the same functional configuration are denoted with the same reference symbol, and redundant description thereof will be omitted.

Note that the description will be made in the following order.

1. Observation range in intraocular observation
2. System configuration
3. Image processing
3.1. Image integration processing
(1) Image acquisition
   Image acquisition by surgical microscope
   Image acquisition by tomographic acquisition device
   Image acquisition by intraocular endoscope
   Image acquisition by illustration generating device
(2) Generation of integrated image
3.2. Presentation image generation processing
   Flattening solid integrated image
   Geometric transformation processing
   Image work indicating type of original image
   Integrated image and single image arranged side by side
4. Hardware configuration
5. Conclusion

1. OBSERVATION RANGE IN INTRAOCULAR OBSERVATION

In retinal surgical operations, while there is a demand for always observing a wide range simultaneously in order to determine retinal traction by the vitreous body and the like, for example, there is a demand for enlarging and observing the posterior pole when providing treatment for the posterior pole. For example, for posterior pole observation of observing the posterior pole of an eyeball E, a contact lens 10a shown on the left side of FIG. 1 or a non-contact lens (not shown) is used. Meanwhile, for wide-angle observation of observing a fundus of the eyeball E in a wide range, a wide-angle observation lens 10b and the like shown on the right side of FIG. 1 is used. The wide-angle observation lens 10b is provided in a surgical microscope as an additional optical system, for example, in a wide-angle observation system for observing a real image created by the additional optical system.

Figure 2:
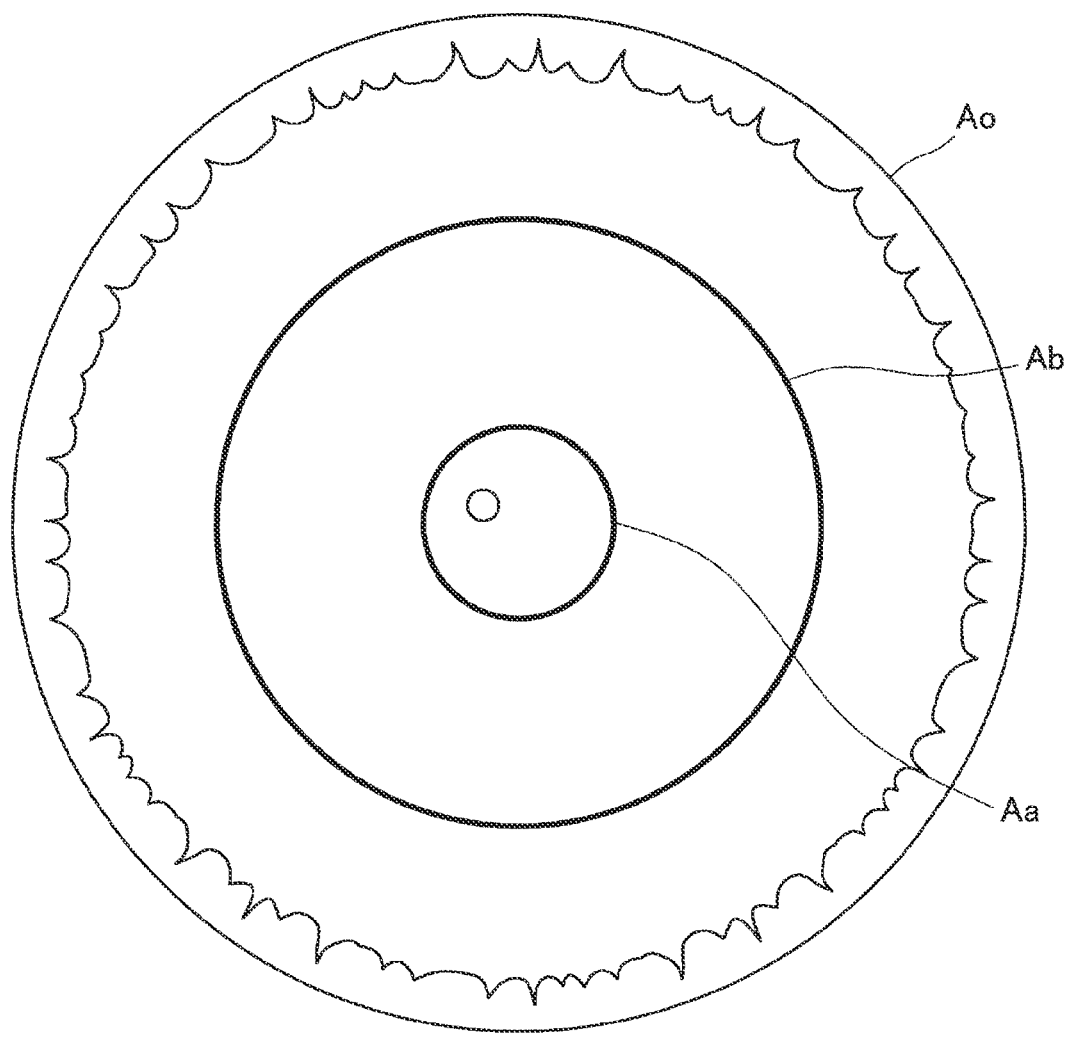
FIG. 2 is an explanatory diagram showing an observation range of the posterior pole observation and an observation range of the wide-angle observation with respect to a fundus range represented by flattening a fundus part of an eyeball.

FIG. 2 shows an observation range Aa of posterior pole observation and an observation range Ab of wide-angle observation with respect to a fundus range Ao represented by flattening a fundus part of an eyeball. As shown in FIG. 2, the observation range Ab in wide-angle observation using the wide-angle observation lens 10b is wider than the observation range Aa in posterior pole observation using the contact lens 10a. Note that for the sake of convenience, FIG. 2 shows only the optic disc and the ora serrata as features of the retina, and this is similar in FIGS. 4 and 17 as described later.

As shown on the right side of FIG. 1, the use of the surgical microscope and the wide-angle observation system makes it possible to simultaneously observe the inside of the eye in a wide range to some extent. However, even if the surgical microscope and the wide-angle observation system are used, it is difficult to simultaneously observe a wider range including, for example, an ora serrata 58, which is a boundary between a photoreception portion of a retina 57 (pars optica retinae) and a non-photoreception portion (pars caeca retinae or pars ciliaris retinae), or a pars plana 59.

Therefore, it is also considered to observe a portion that is difficult to observe in a case where the surgical microscope and the wide-angle observation system are used from an image acquired by an image generating device including an intraocular endoscope, an optical coherence tomography (OCT), or the like. For example, if the intraocular endoscope is used, it is possible to observe the pars plana 59 and the like. If the OCT is used, for example, even in a case where the retina 57 cannot be observed with the surgical microscope because see-through is difficult with visible light, a retinal image can be acquired in some cases. However, in an image obtained with the intraocular endoscope, a range in which simultaneous observation is possible is extremely limited. Furthermore, in a case where the OCT is used, it is currently difficult to obtain an observation range equivalent to an observation range of the surgical microscope.

Furthermore, in order to switch between the posterior pole observation and the wide-angle observation as shown in FIG. 1, the lens to use needs to be changed, and the observation range in the posterior pole observation and the observation range in the wide-angle observation cannot be observed simultaneously. It also takes time to change the lens.

Moreover, in a case where the wide-angle observation lens 10b as in the right side of FIG. 1 is used, in an intraocular image presented to an operator, the retina, which is originally close to a spherical surface, looks planar. Therefore, in a case where an unskilled operator looks at the intraocular image, there is a risk of a wrong operation in which the operator who recognizes that the retina is a plane moves a surgical tool and hits the surgical tool against the retina. Furthermore, characteristics of image distortion in the image observed by the operator are determined by the optical system used during the observation, especially in the surgical microscope, which is not necessarily desirable for a user.

Figure 3:
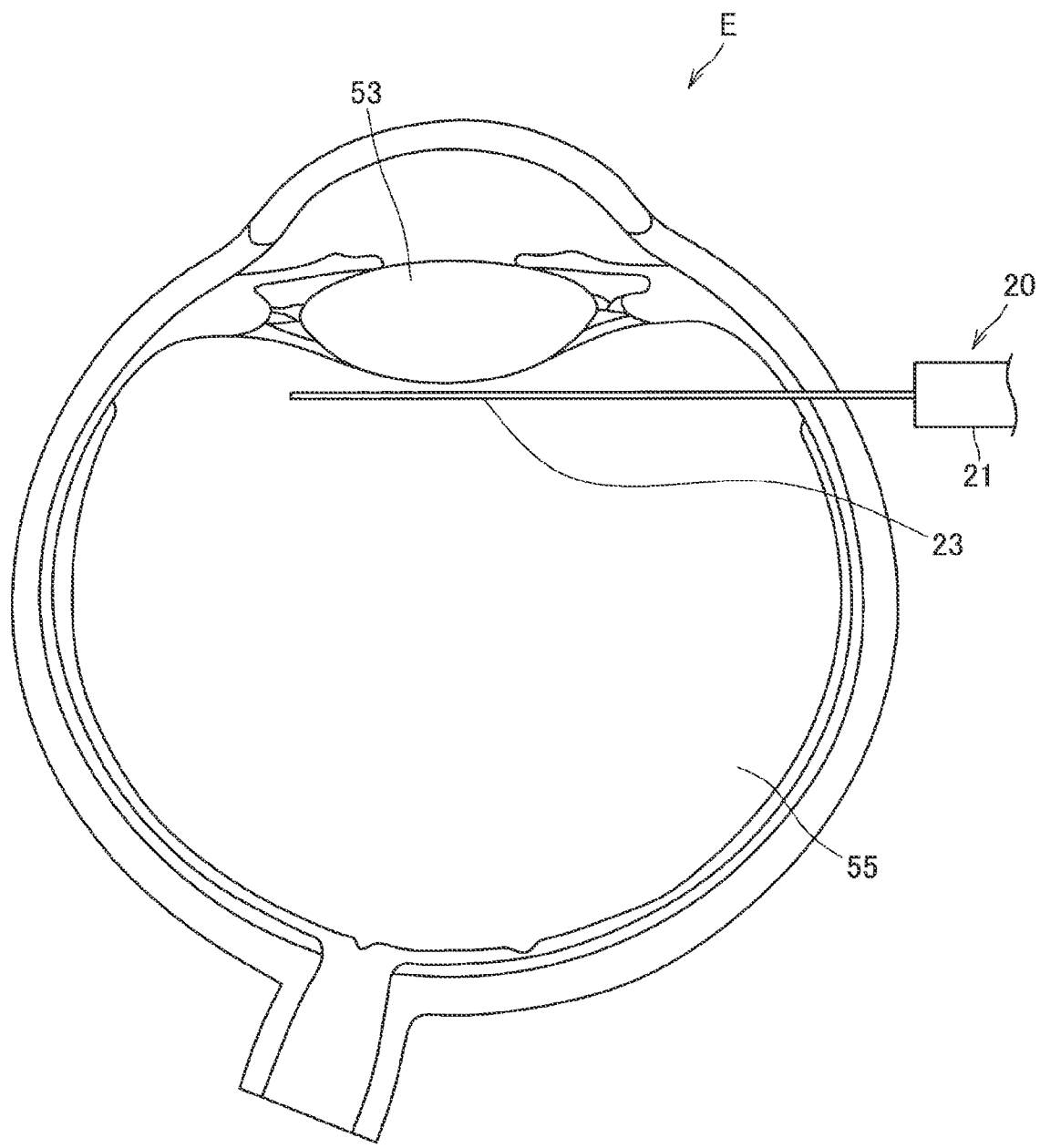
FIG. 3 is an explanatory diagram showing an example of use of intraocular observation by an intraocular endoscope.
Figure 4:
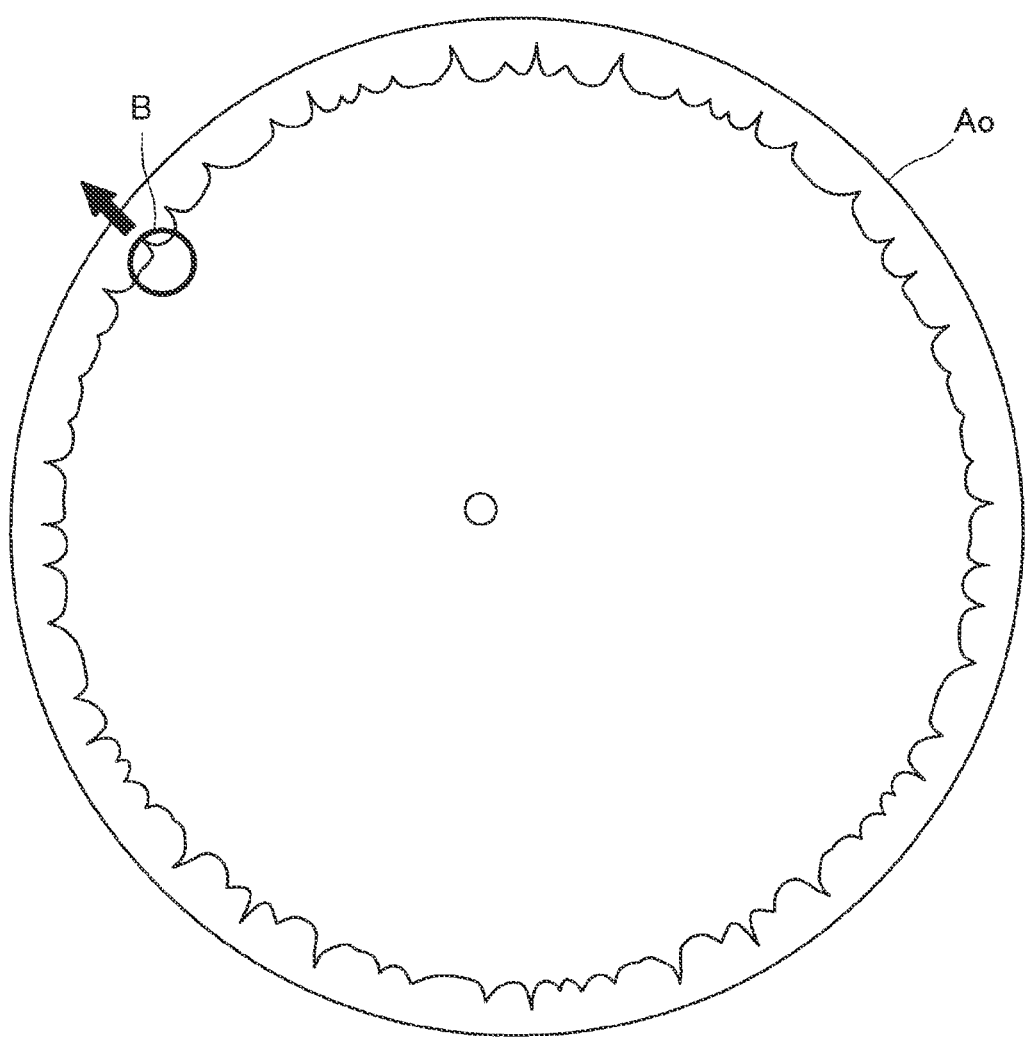
FIG. 4 is an explanatory diagram showing a display example of a position and direction of the intraocular endoscope of FIG. 3.

Furthermore, when the intraocular endoscope is used during observation of an intermediate translucent body opaque eye or during observation of a peripheral portion, the range of image to be acquired is determined from a tip position and direction of an endoscope probe with respect to the eyeball, and from a posture of the endoscope probe represented by a rotation angle around an optical axis. However, it is difficult to determine the posture of the endoscope probe from the image captured by the intraocular endoscope. Therefore, using the intraocular endoscope requires a high degree of skill. For example, as shown in FIG. 3, it is assumed that an intraocular endoscope 20 is inserted into a vitreous body 55 of the eyeball E from the right side of sheet of FIG. 3 at a predetermined rotation angle such that a tip 23 extending from a grip portion 21 of the intraocular endoscope 20 is located near a crystalline lens 53. At this time, even if a range B is captured by the intraocular endoscope 20 such that a direction of an arrow is upward in the image as shown in FIG. 4, it is difficult to understand this from the captured image.

Therefore, in view of the above, an intraocular image processing system of the present disclosure enables intraocular observation in a wider range and at the same time in a desirable way for the operator.

2. SYSTEM CONFIGURATION

Figure 5:
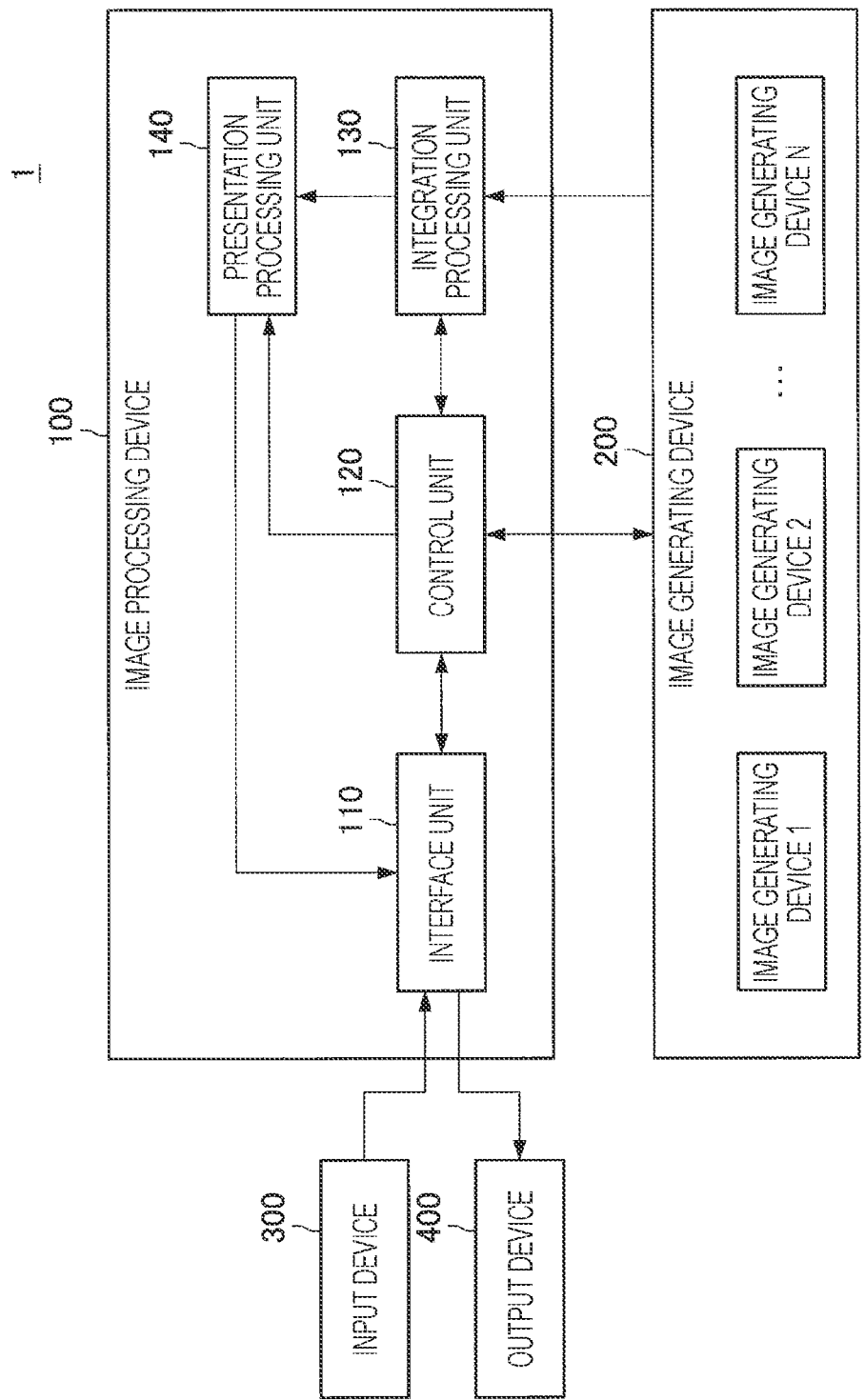
FIG. 5 is a block diagram showing one configuration example of an intraocular image processing system according to one embodiment of the present disclosure.

To begin with, with reference to FIG. 5, a configuration of an intraocular image processing system 1 according to one embodiment of the present disclosure will be described. FIG. 5 is a block diagram showing one configuration example of the intraocular image processing system 1 according to the present embodiment. As shown in FIG. 5, the intraocular image processing system 1 according to the present embodiment includes an image processing device 100, a plurality of image generating devices (hereinafter, the plurality of image generating devices will be collectively described as "image generating devices 200"), an input device 300, and an output device 400.

(Image Processing Device)

The image processing device 100 includes an interface unit 110, a control unit 120, an integration processing unit 130, and a presentation processing unit 140.

The interface unit 110 is a functional unit that exchanges information with a user of the intraocular image processing system 1. For example, the interface unit 110 outputs an instruction to the system input by the user via the input device 300 to the control unit 120. Furthermore, for example, the interface unit 110 outputs a state of the system to the output device 400 to notify the user.

The control unit 120 controls the image processing device 100 on the basis of the instruction from the user, and executes processing such as image integration or generation of a presentation image in an appropriate mode. In addition to the image processing device 100, the control unit 120 may control other components of the intraocular image processing system 1 including the image generating devices 200 and the like. For example, the control unit 120 may perform control such that image acquisition by the image generating devices 200 is appropriately performed.

The integration processing unit 130 integrates images generated by the image generating devices 200 by correlating intraocular positions, and generates one integrated image indicating intraocular information in a range wider than the image range of each image. The integration processing unit 130 may perform alignment between images, for example, on the basis of image features included in the images generated by the image generating devices 200. Furthermore, when integrating the images generated by the image generating devices 200, in addition to information obtained from these images, with reference to control information of the image generating devices 200 and the like, the integration processing unit 130 may estimate a posture of the eye or the endoscope, or may estimate a solid shape of the eye. The integration processing unit 130 outputs the generated integrated image to the presentation processing unit 140.

The presentation processing unit 140 processes the integrated image according to a presentation format of the integrated image to generate a presentation image. The presentation processing unit 140 performs image work including projective transformation, geometric transformation, color transformation, and the like on the integrated image on the basis of an instruction from the control unit 120. The presentation processing unit 140 outputs the generated presentation image to the output device 400 via the interface unit 110.

(Image Generating Device)

The image generating devices 200 are devices that generate images to be integrated by the image processing device 100 in the intraocular image processing system 1. The image generating devices 200 include at least a device that can generate an ophthalmologic image that is an intraoperatively acquired image acquired during an intraocular ophthalmologic surgical operation (so-called modality). The image generating devices 200 are specifically ophthalmologic observation devices including a surgical microscope, a tomographic acquisition device, an intraocular endoscope, or the like. Furthermore, the image generating devices 200 may each include an illustration generating device and the like that generates an illustration in which the fundus is illustrated. The image generating devices 200 are, for example, controlled by the control unit 120 of the image processing device 100, acquire images, and generate images. The generated images are input into the integration processing unit 130.

(Input Device)

The input device 300 is a device for the user to input instruction information into the intraocular image processing system 1. The input device 300 includes, for example, an input unit for the user to input information including a mouse, a keyboard, a touch panel, a button, a microphone, a switch, a lever, and the like, an input control circuit that generates an input signal on the basis of the input by the user and outputs the input signal to a CPU, and the like.

(Output Device)

The output device 400 is a device that displays the presentation image. The output device 400 may be, for example, a display device including a liquid crystal display (LCD) device, an organic light emitting diode (OLED) device, and the like. Furthermore, the output device 400 may include a voice output device including a speaker and the like.

3. IMAGE PROCESSING

Figure 6:
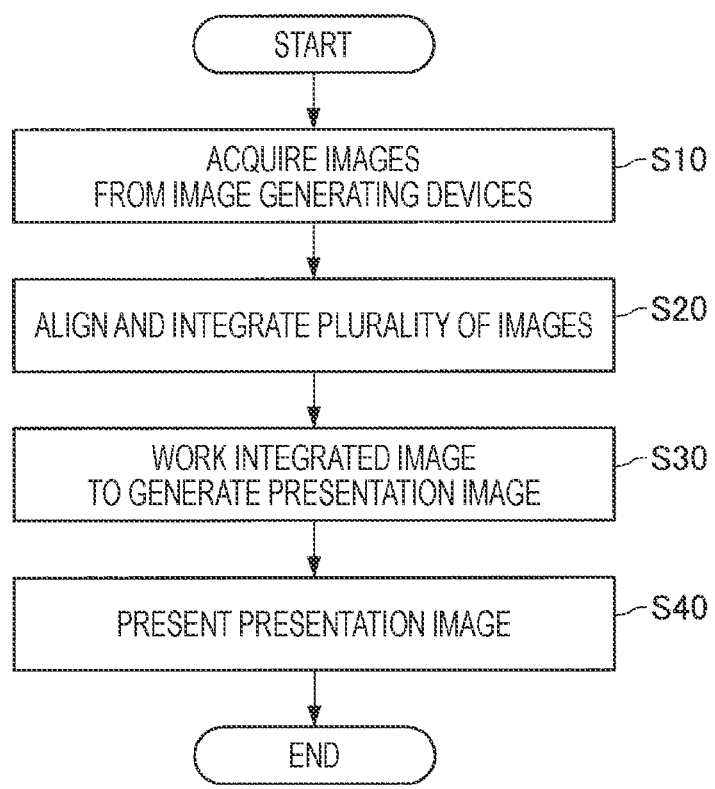
FIG. 6 is a flowchart showing a flow of image integration processing and presentation image generation processing by the intraocular image processing system according to the embodiment.

Next, with reference to FIG. 6, image integration processing and presentation image generation processing by the intraocular image processing system 1 will be described. FIG. 6 is a flowchart showing a flow of the image integration processing and the presentation image generation processing by the intraocular image processing system 1 according to the present embodiment. The processing shown in FIG. 6 is executed by the image processing device 100 of the intraocular image processing system 1.

[3.1. Image Integration Processing]

To begin with, the image processing device 100 acquires images generated by the image generating devices 200 (S10), and generates one integrated image from the acquired images (S20).

Figure 7:
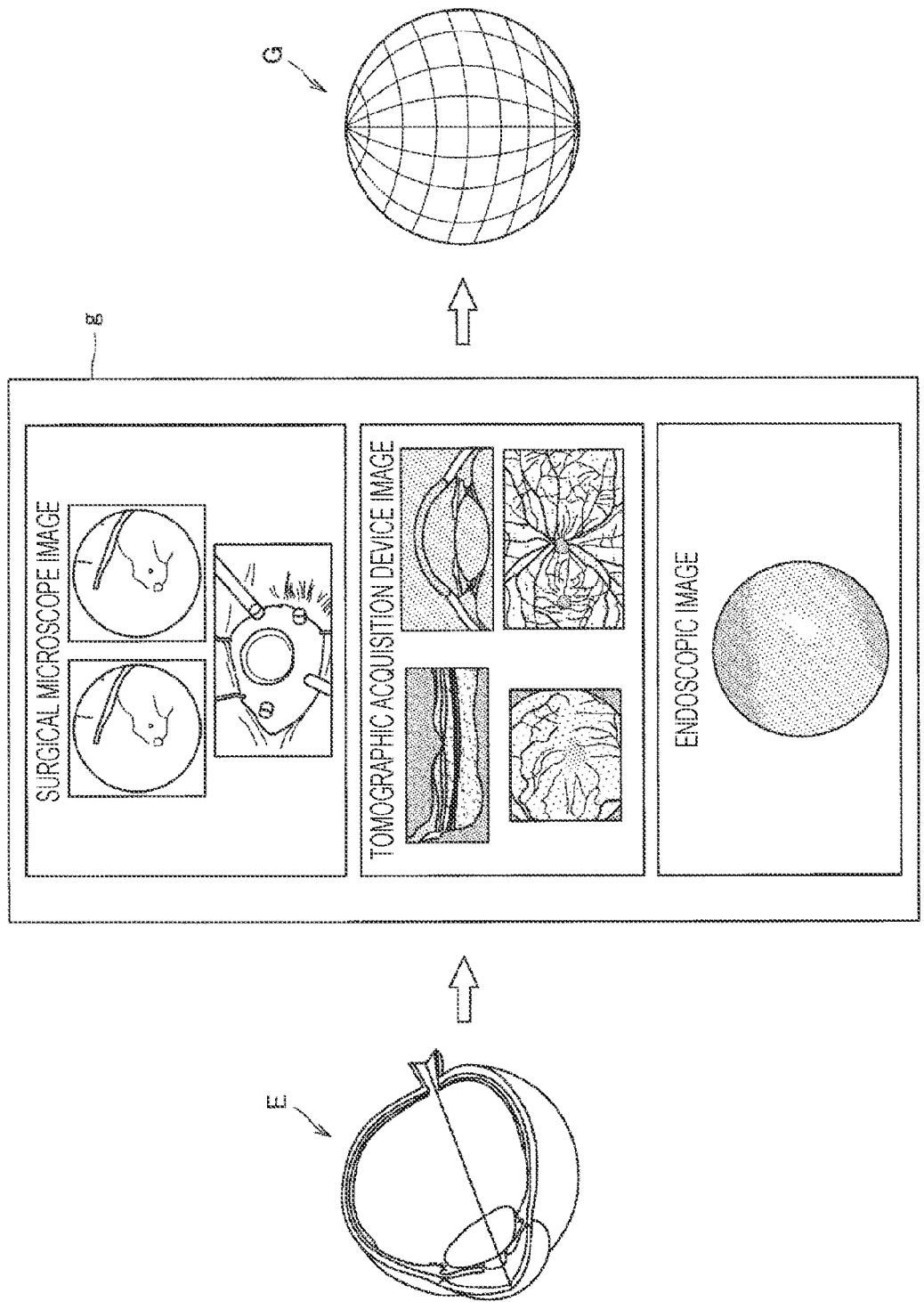
FIG. 7 is an explanatory diagram showing generation processing of a three-dimensional integrated image.
Figure 8:
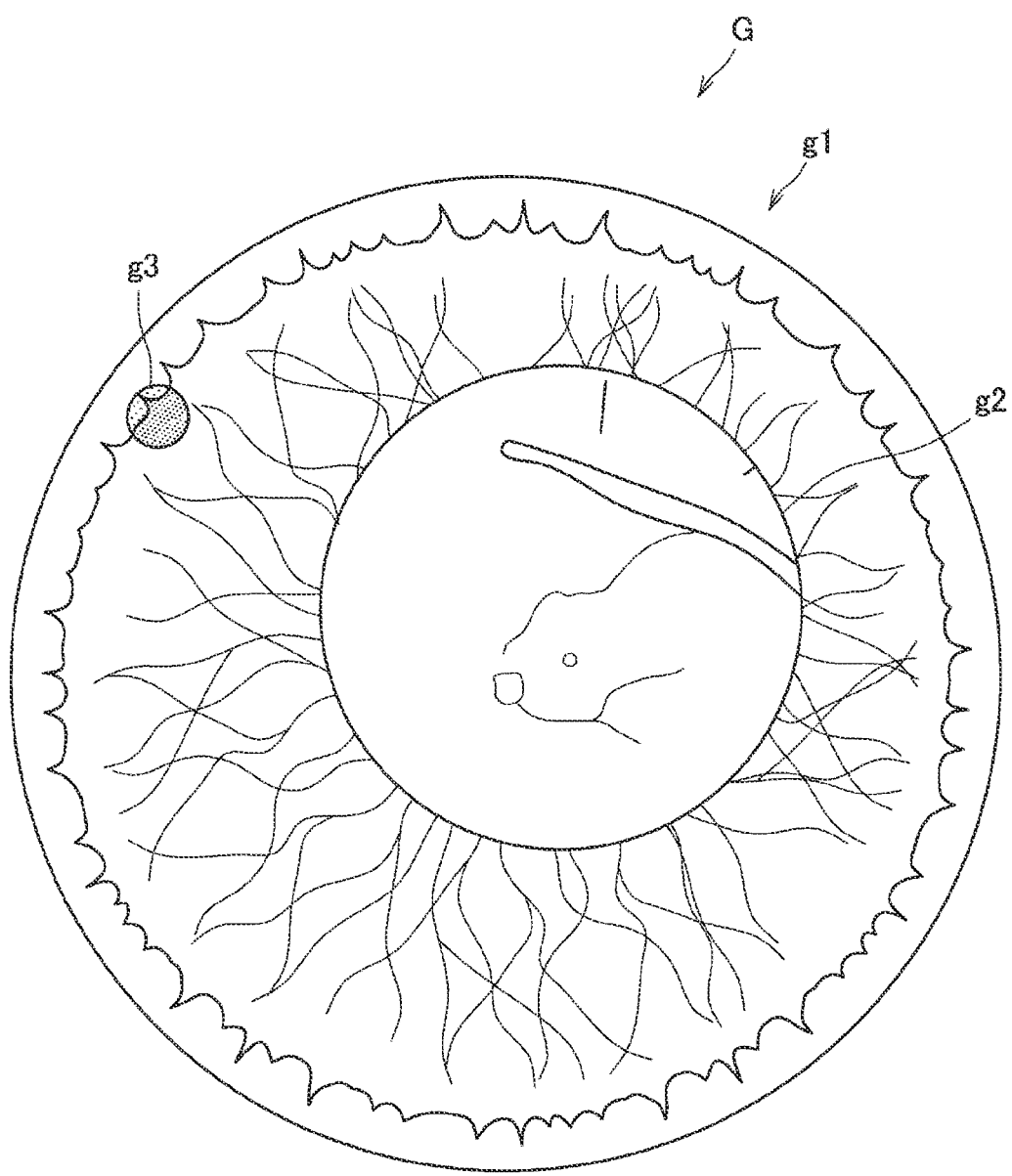
FIG. 8 is an explanatory diagram showing one example of a two-dimensional integrated image.

Before detailed description of the image integration processing, an outline of the image integration processing will be described with reference to FIGS. 7 and 8. FIG. 7 is an explanatory diagram showing generation processing of a three-dimensional integrated image. FIG. 8 is an explanatory diagram showing one example of a two-dimensional integrated image.

The integrated image is generated on the basis of the images acquired from the eyeball by the image generating devices 200. For example, the image generating devices 200 receive an instruction from the control unit 120 and acquire intraocular information. With this operation, for example, as shown in FIG. 7, surgical microscope images acquired by the surgical microscope, tomographic acquisition device images acquired by the tomographic acquisition device, endoscopic images acquired by the intraocular endoscope, or the like are generated. On the basis of these images and control information of the image generating devices 200 by the control unit 120 as necessary, the integration processing unit 130 integrates the images to generate an integrated image G.

The integrated image G may be a solid three-dimensional integrated image as shown in FIG. 7, or may be a planar two-dimensional integrated image as shown in FIG. 8. The integrated image G of FIG. 8 is an image in which an illustration g1 of the fundus generated by the illustration generating device, a surgical microscope image g2, and an endoscopic image g3 are integrated. Generation of such an integrated image obtained by integrating the plurality of images into one image makes it possible to simultaneously observe a wider range than an intraocular range indicated by the image generated by each image generating device. The image integration processing will be described in detail below.

(1) Image Acquisition

For example, it is assumed that a request for presenting the integrated image from the user of the intraocular image processing system 1 is input from the input device 300. On receipt of the presentation request of the integrated image via the interface unit 110, the control unit 120 of the image processing device 100 notifies the image generating devices 200 of an image generation instruction, and causes the image generating devices 200 to output the generated images to the integration processing unit 130 (S10).

As the image generating devices 200, for example, a surgical microscope, a tomographic acquisition device, an intraocular endoscope, an illustration generating device, and the like are used.

(Image Acquisition by Surgical Microscope)

The surgical microscope is a microscope that observes the inside of the eye from a pupil and magnifies and presents a real image in an ophthalmologic surgical operation. The surgical microscope includes an image capturing device for acquiring a microscope image. The range of the image acquired by the image capturing device included in the surgical microscope differs depending on the optical system as shown in FIG. 1. For example, for posterior pole observation, an image of a relatively narrow range in the eye is acquired, and for wide-angle observation, an image of a relatively wide range in the eye is acquired.

Figure 9:
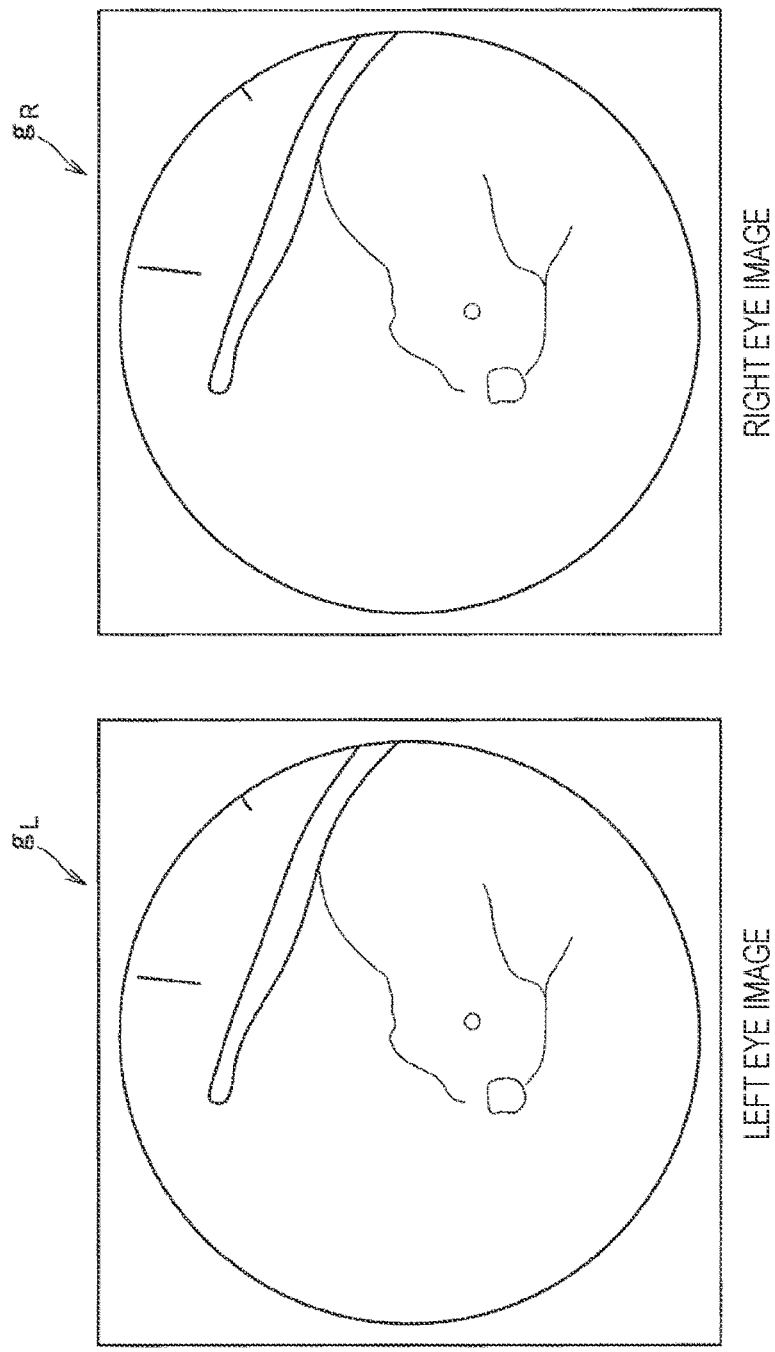
FIG. 9 is an explanatory diagram showing a right eye image and a left eye image captured by an image capturing device mounted on a surgical microscope.
Figure 10:
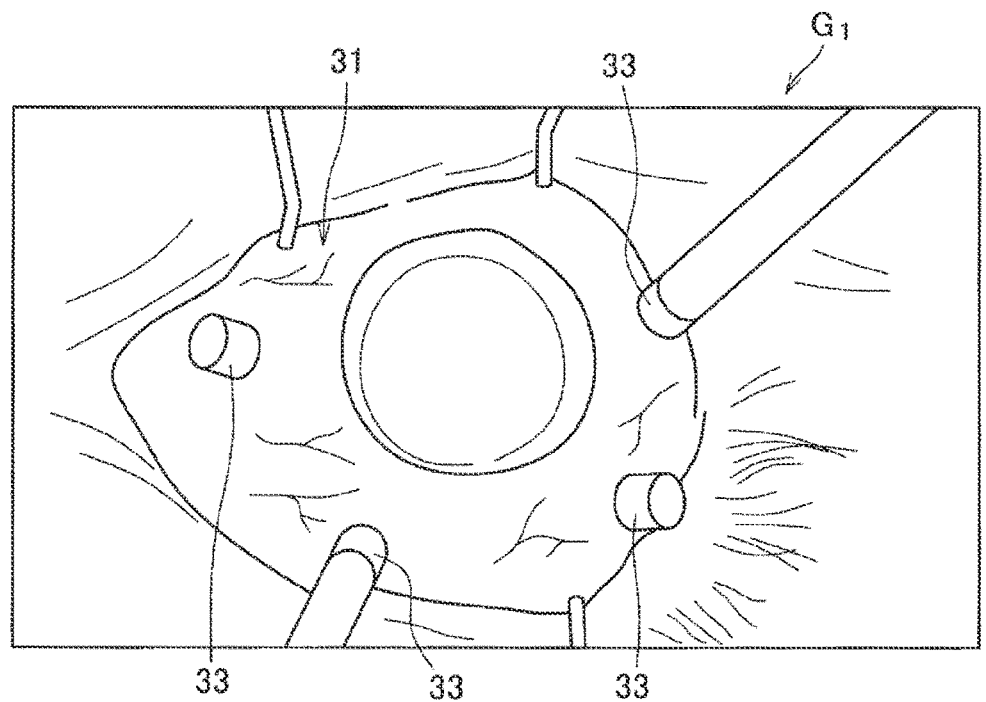
FIG. 10 is an explanatory diagram for describing an image feature for estimating a posture of an eye in a surgical microscope image.

The image capturing device may include a right eye camera and a left eye camera to enable images observed by the surgical microscope to be stereoscopically viewed. In this case, for example, as shown in FIG. 9, a right eye image $g_R$ captured by the right eye camera and a left eye image $g_L$ captured by the left eye camera are acquired. From a parallax obtained on the basis of the right eye image $g_R$ and the left eye image $g_L$, for example, it is also possible to estimate a solid shape of the retina of the eyeball. Furthermore, on the basis of the surgical microscope image, it is also possible to estimate the posture of the eye. For example, as shown in FIG. 10, it is possible to estimate the posture of the eye with respect to the surgical microscope by storing the position of the image feature including a corneal limbal blood vessel 31, a trocar 33, and the like in a situation where the eyeball is facing the surgical microscope when a surgical operation starts and observing subsequent change in the position of the image feature.

(Image Acquisition by Tomographic Acquisition Device)

The tomographic acquisition device is a device that acquires a tomogram of the eyeball. For example, the OCT, an ultrasound device such as an ultrasound biomicroscope (UBM), or the like may be used. Hereinafter, a case where the OCT is used as one example of the tomographic acquisition device will be described.

Figure 11:
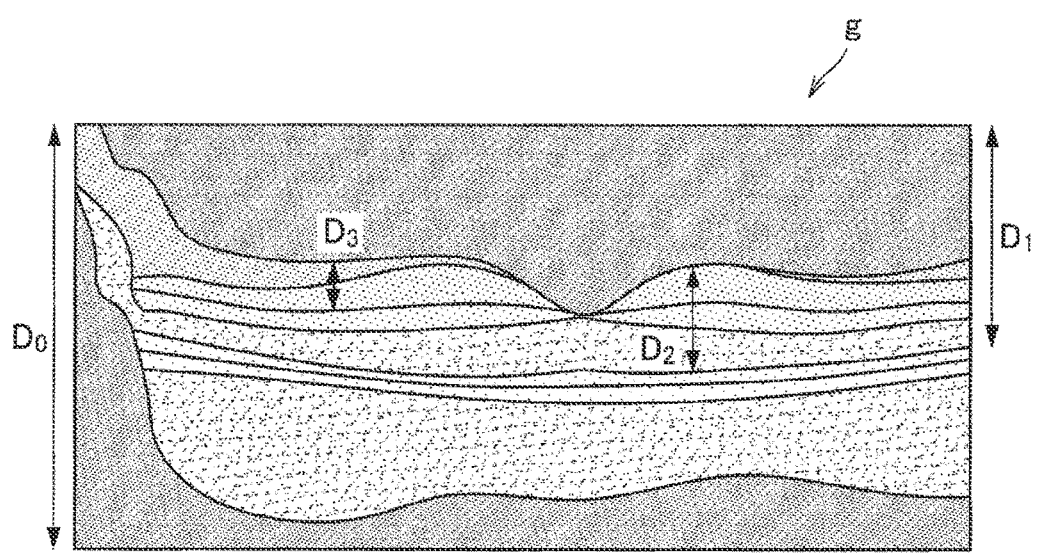
FIG. 11 is an explanatory diagram for describing a depth range to be used for generating a front image in a tomogram acquired by a tomographic acquisition device.
Figure 12:
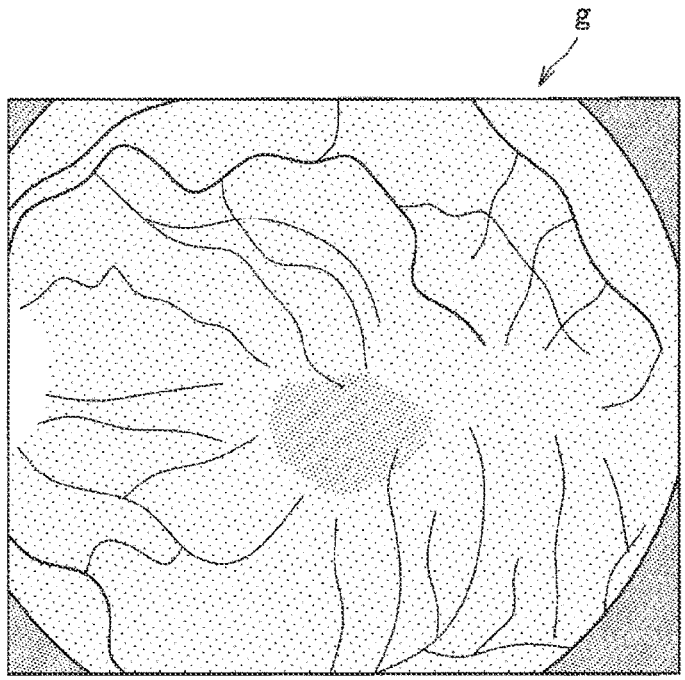
FIG. 12 is an explanatory diagram showing one example of the front image generated from the tomogram acquired by the tomographic acquisition device.

The OCT can acquire a front image of the eyeball by acquiring a tomogram as volume data and generating a so-called enFace image on the basis of such data. The enFace image is generated by taking an average, maximum, minimum, or the like of luminance values in a depth range set in advance. As the depth range to be used to generate the enFace image, all depths ($D_0$) may be used in an image g of a tomogram shown in FIG. 11, and a depth ($D_1$) constant regardless of a retina region may be used. Furthermore, in the image g of a tomogram, a depth in a range of a specified region (layer) of the retina may be used, for example, a depth from an inner limiting membrane to an outer limiting membrane ($D_2$), a depth from the inner limiting membrane to an inner plexiform layer ($D_3$), and the like. From such an image of tomogram, for example, the front image of the eyeball shown in FIG. 12 is acquired as the image g acquired by the image generating device.

Figure 13:
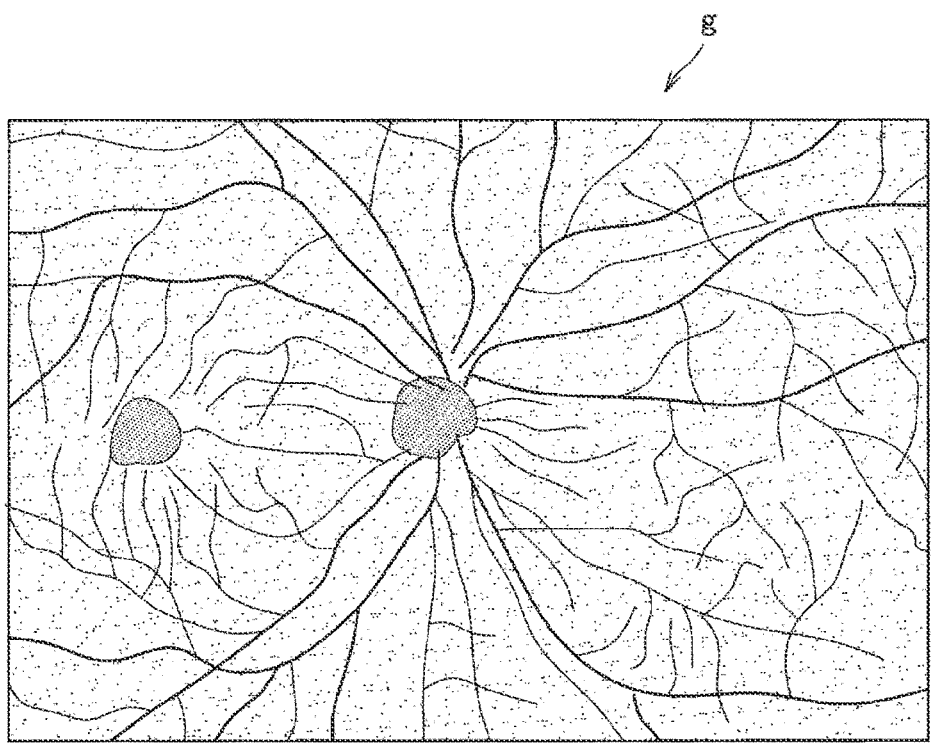
FIG. 13 is an explanatory diagram showing one example of a vascular plexus image generated from the tomogram acquired by the tomographic acquisition device.

Furthermore, as the front image in the OCT, as shown in FIG. 13, for example, it is possible to acquire one or more vascular plexus images that can be acquired by OCT angiography. Such a vascular plexus image may be used as the image g acquired by the image generating device.

Figure 14:
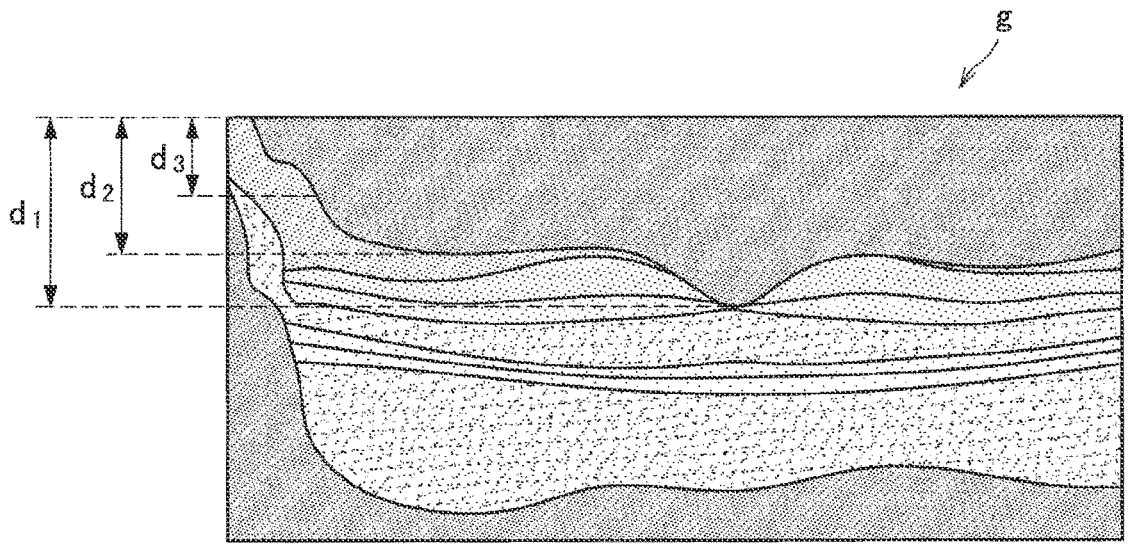
FIG. 14 is an explanatory diagram showing retinal depth information obtained from the tomogram acquired by the tomographic acquisition device.

Note that the solid shape of the retina can also be estimated on the basis of a depth position of the retina acquired from the image g of the OCT tomogram. For example, as shown in FIG. 14, a plurality of depths (for example, $d_1$, $d_2$, $d_3$) from an upper end of the image g to the inner limiting membrane of the retina in a direction along a surface of the retina is acquired. The solid shape of the retina is estimated from the change in the depth position of the retina.

Figure 15:
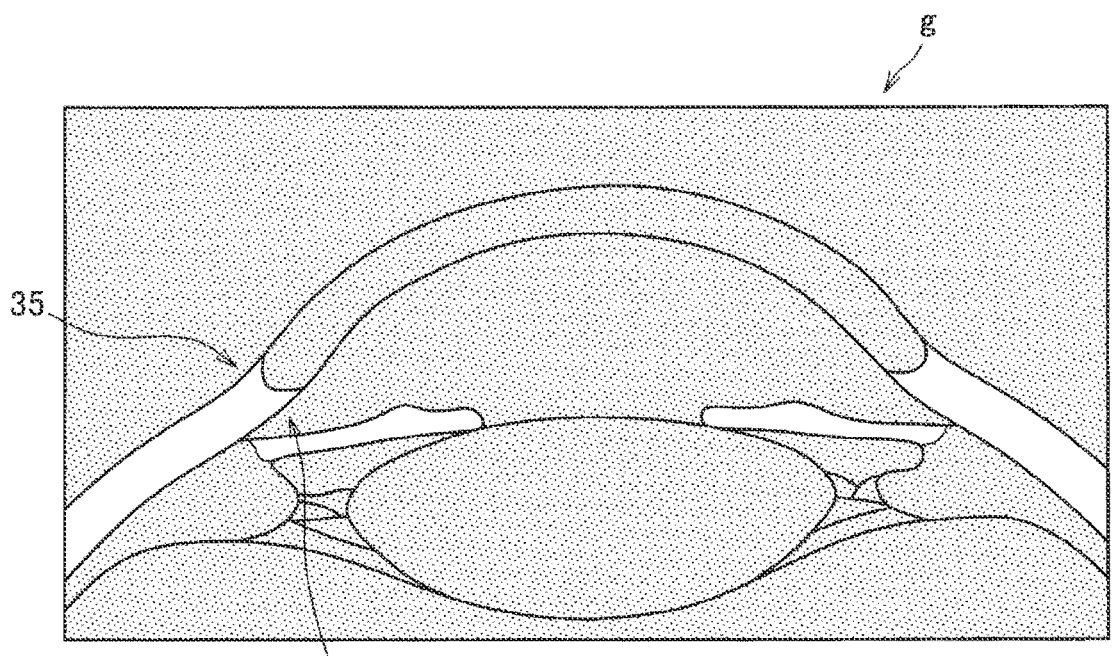
FIG. 15 is an explanatory diagram showing an example of a position of a specified region of the eye obtained from the tomogram acquired by the tomographic acquisition device.

Furthermore, the posture of the eye with respect to the OCT can also be estimated on the basis of the position of the specified region acquired from the image g of the OCT tomogram. For example, as shown in FIG. 15, it is possible to measure the position of a corneal limbus 35 or an iridocorneal angle 37 and estimate the posture of the eye with respect to the OCT on the basis of a measurement result. Note that in a case where the OCT tomogram is acquired as volume data, the corneal limbus 35 and the iridocorneal angle 37 are distributed in a ring shape.

Information regarding the estimated solid shape of the retina and the posture of the eye with respect to the OCT may be used in the generation processing of the integrated image.

(Image Acquisition by Intraocular Endoscope)

The intraocular endoscope is a surgical tool for observing the inside of the eyeball. The intraocular endoscope emits illumination light from the tip of an insertion portion that is inserted into the eye, illuminates a portion to be captured, and captures an image of the inside of the eye. The image captured by the intraocular endoscope can be integrated into the integrated image.

Figure 16:
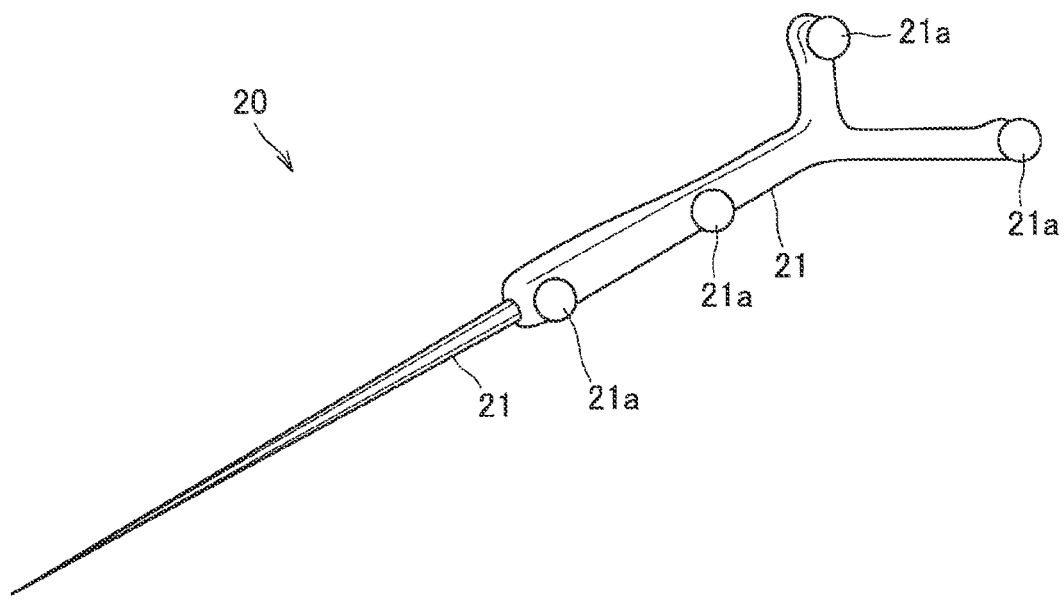
FIG. 16 is a schematic explanatory diagram showing the intraocular endoscope in which a three-dimensional marker is attached to a grip portion.
Figure 17:
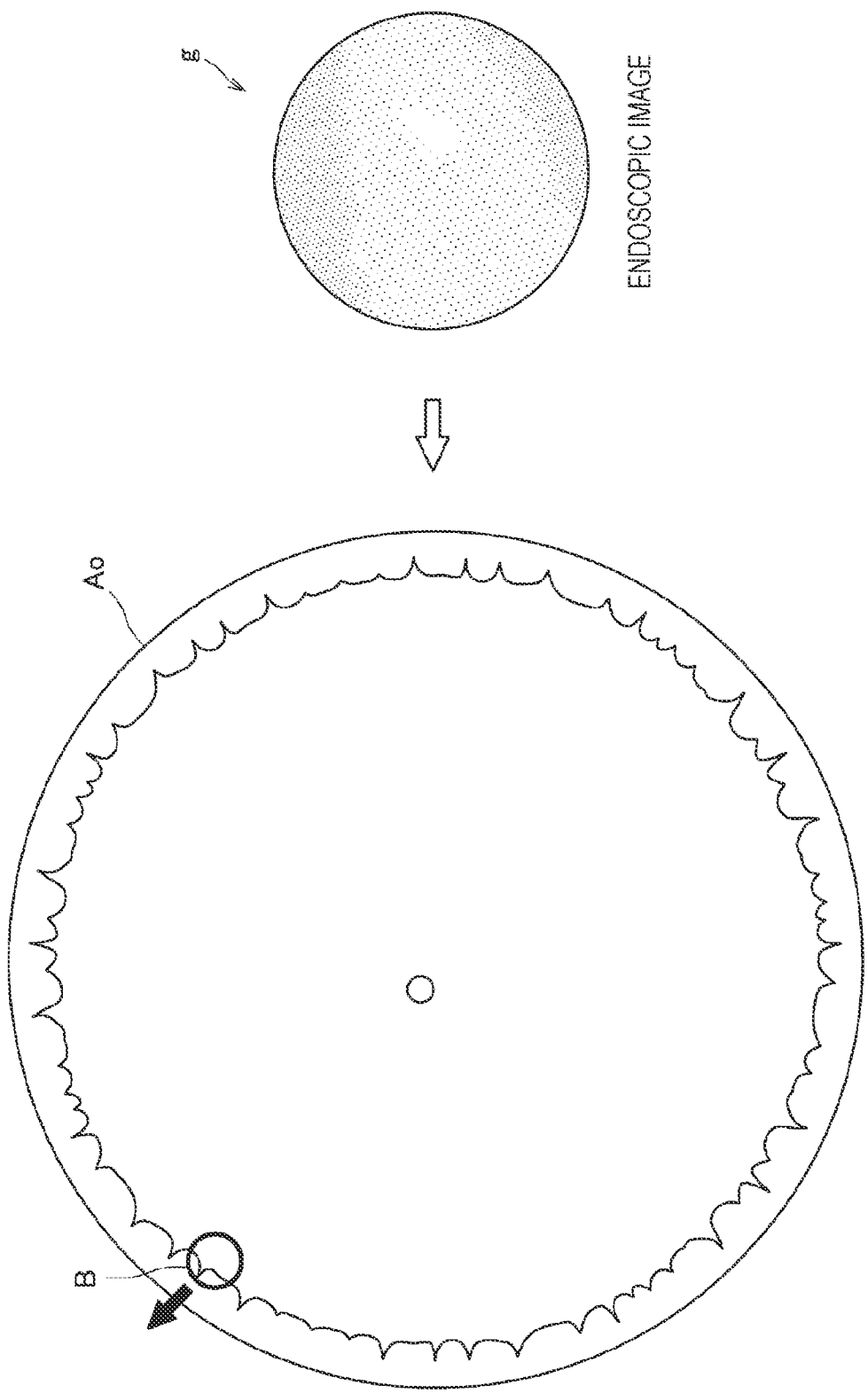
FIG. 17 is an explanatory diagram showing one example of an endoscopic image, and a range and direction of the endoscopic image with respect to the fundus range identified from an estimation result of a posture of the intraocular endoscope when the endoscopic image is acquired.

When integrating the endoscopic image, a posture estimation result of the endoscope with respect to the eye may be used. Specifically, by estimating a range and direction of the image captured by the intraocular endoscope on the retina, on the basis of the estimation result, it is possible to perform alignment with an image generated by another image generating device. The posture of the intraocular endoscope with respect to the eye may be estimated, for example, on the basis of the estimation result of the posture of the eye based on the surgical microscope image and the estimation result of the posture of the intraocular endoscope (for example, Patent Document 1). At this time, for example, as shown in FIG. 16, the intraocular endoscope 20 in which a three-dimensional marker 21a for identifying the rotation angle or position is attached to the grip portion 21 is used and measurement is performed with an optical tracking system, thereby making it easier to acquire robust results. FIG. 17 shows one example of the endoscopic image (image g) acquired by the intraocular endoscope 20, and the range B and direction of the endoscopic image with respect to the fundus range Ao identified from the estimation result of the posture of the intraocular endoscope 20 when the endoscopic image is acquired. An arrow on the left side of FIG. 17 indicates the direction to which the upward direction of the endoscopic image on the right side of FIG. 17 corresponds.

(Image Acquisition by Illustration Generating Device)

Figure 18:
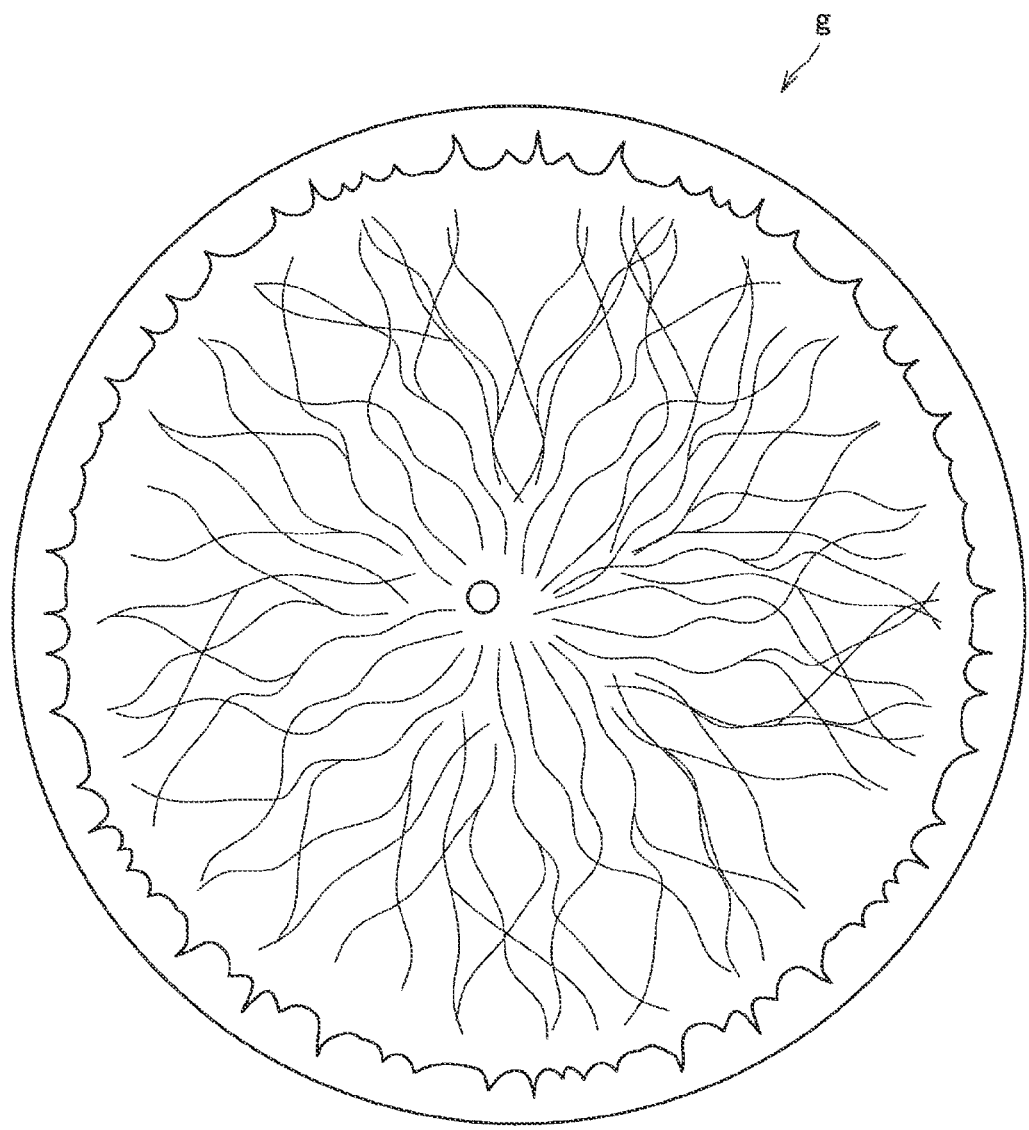
FIG. 18 is an explanatory diagram showing one example of an illustration showing the fundus.

The surgical microscope, the tomographic acquisition device, and the intraocular endoscope described above are each a modality that can acquire the ophthalmologic image. An image other than the ophthalmologic image may be used as an image to be integrated into the integrated image. For example, the illustration generating device may be used to generate an illustration that illustrates intraocular information, and the illustration may be used as the image g to be integrated into the integrated image. For example, as shown in FIG. 18, an illustration representing the fundus may be generated by the illustration generating device. At this time, the illustration generating device may generate the illustration, for example, on the basis of average fundus information obtained by dissection, or may generate the illustration on the basis of information acquired about the eye of a patient.

Note that the illustration generated on the basis of the average fundus information obtained by dissection does not always agree with the fundus of the patient's eye. Therefore, in a case where such an illustration is integrated into the integrated image, for example, geometric transformation may be performed on the basis of the information acquired about the patient's eye so as to agree with the image acquired by another image generating device.

In this way, respective images g acquired by the image generating devices 200 on the basis of the instruction from the control unit 120 are output to the integration processing unit 130.

(2) Generation of Integrated Image

Next, the integration processing unit 130 generates one integrated image G from the images g acquired by the image generating devices 200 (S20). The images g are integrated by correlating the intraocular positions.

To begin with, the integration processing unit 130 uses the image g acquired from one arbitrary image generating device 200 as a reference image. Then, the integration processing unit 130 aligns the image g acquired by another image generating device 200 with an image shape of the reference image, and integrates these images g, for example, after further performing transformation processing and the like including affine transformation and the like. For example, in the integrated image G shown in FIG. 8, the illustration g1 of the fundus generated by the illustration generating device is used as a reference image. The surgical microscope image g2 and the endoscopic image g3 are integrated on the basis of region positions of the eye, for example, the central fovea, the ora serrata, and the like.

The images g to be integrated into the integrated image G are not limited to the current ophthalmologic images, and for example, past images acquired by the image generating devices 200 may be used. In a case where images from a plurality of image generating devices and furthermore past images are integrated, a plurality of images at the same position in the eye may exist. In this case, one image may be generated by performing weighted addition of images according to identity of the images, and only one image may be selected and used from among the plurality of images. For example, in a case where weighted addition of images is performed on a past image, the weight of the image may be reduced, and in a case where only one image is selected from among a plurality of images, the priority of selection may be lowered. It is expected that a good image will be obtained for the user by performing such processing.

Furthermore, for example, in a case where the solid integrated image G as shown in FIG. 7 is generated, for example, the posture of the eye, the depth of the retina, and the posture of the intraocular endoscope may be estimated from the images g, and the images g may be integrated on the basis of estimation results. Alternatively, the integration processing unit 130 may recognize the image feature of each image g and estimate the positional relationship of the plurality of images from position distribution of the recognized image feature. The positions of the plurality of images g can also be aligned on the basis of such an estimation result. As the image feature, for example, macro information such as positions of regions including the optic disc, central fovea, ora serrata, and the like may be used, or micro information such as a branch point of a blood vessel may be used.

Furthermore, in a case where the integrated image G is built into a solid retinal image, as a shape of the retina, for example, a perfect sphere model may be used, an average retina shape model may be used, and a solid model of the patient's eye restored on the basis of the solid information obtained from the images g may be used. Note that to estimate distortion of a front image generated by each image generating device 200 and to estimate the shape of the retina, a model regarding optical characteristics of the intermediate translucent body including the optical system used for each image generating device 200 and the like may be used.

In this way, the images g acquired by respective image generating devices 200 are integrated to generate one integrated image G. The integrated image G shows a wider range than a range of at least an ophthalmologic image acquired by a modality including the surgical microscope, the tomographic acquisition device, the intraocular endoscope, and the like out of respective image generating devices 200. Such an integrated image G makes it possible to simultaneously present wide-range intraocular information that is not obtained with only one modality.

[3.2. Presentation Image Generation Processing]

Returning to the description of FIG. 6, when the integrated image G is generated by the integration processing unit 130, the presentation image is generated by the presentation processing unit 140 (S30). Thereafter, the presentation image is presented to the user (S40). The presentation processing unit 140 works the integrated image G to generate the presentation image, thereby making it possible to present to the user a good image that is comfortable and easy to recognize. The presentation processing unit 140 may perform, for example, the following work on the integrated image G.

(Flattening Solid Integrated Image)

Figure 20:
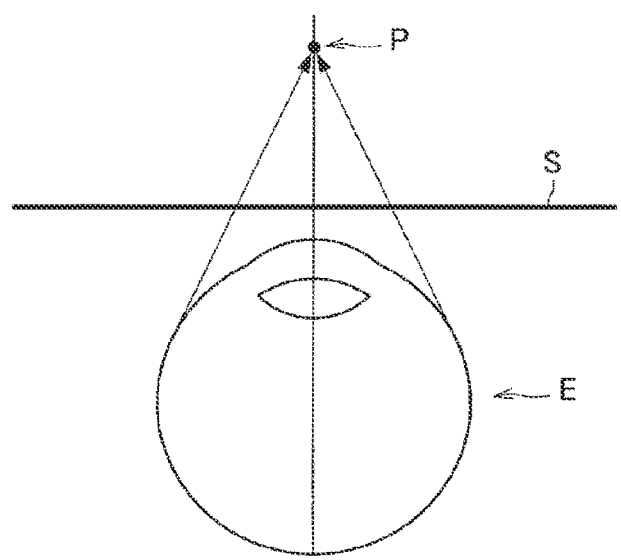
FIG. 20 is an explanatory diagram showing another example of the projection method from the solid image.
Figure 21:
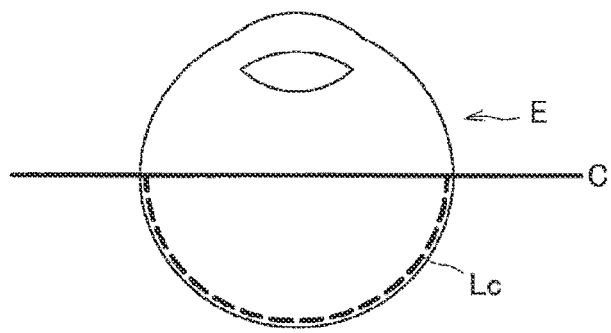
FIG. 21 is an explanatory diagram showing another example of the projection method from the solid image.

In a case where a solid integrated image is generated as the integrated image G, in order to make the presentation image a planar image, it is required at least to project the integrated image G onto a planar image to make the image two-dimensional. As a method of projecting the solid integrated image G, for example, projection methods shown in FIGS. 19 to 21 are considered.

Figure 19:
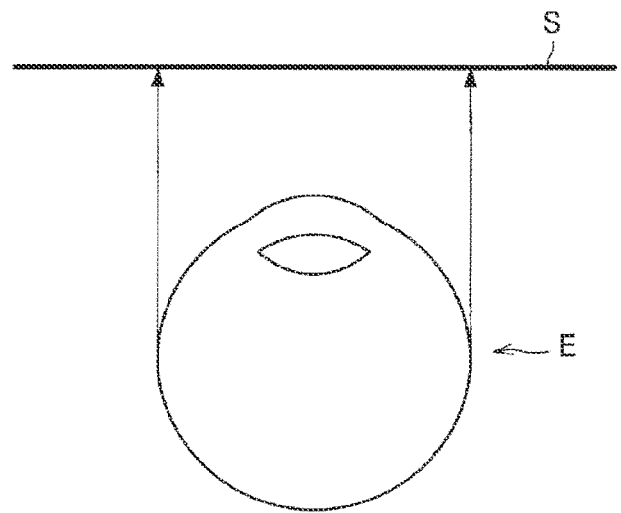
FIG. 19 is an explanatory diagram showing one example of a projection method from a solid image.

For example, as shown in FIG. 19, the solid integrated image G may be orthographically projected on a projection plane S to make a planar image. To orthographically project the integrated image G, it is necessary to determine an angle of the projection plane S with respect to the eye E. Furthermore, for example, as shown in FIG. 20, the solid integrated image G may be perspectively projected on the projection plane S to make a planar image. To perspectively project the integrated image G, it is necessary to determine positions of a viewpoint P and the projection plane S with respect to the eye E. Alternatively, for example, as a method of projecting the solid integrated image G, the integrated image G may be cylindrically projected to make a planar image. That is, the integrated image G is represented by the Mercator projection. To change the integrated image G to a planar image by using the Mercator projection, as shown in FIG. 21, it is necessary to determine a position of a central axis C with respect to the eye E and a line Lc corresponding to 0 degrees longitude.

For the projection plane S, viewpoint P, central axis C, and line Lc of 0 degrees longitude, setting information set in advance on the basis of a mode designated by the user and the like may be used. For example, the projection plane S, viewpoint P, central axis C, and line Lc of 0 degrees longitude may be variable according to the posture of the eye and the position of the surgical tool. For example, if the direction of the optical axis of the surgical microscope with respect to the eye is used as a normal line to the projection plane S, an image that is sensuously close to the image obtained by the surgical microscope is obtained. Such a setting is expected to reduce the user's discomfort with the presentation image. Furthermore, by setting a perpendicular line from the surgical tool to the retina as a normal line to the projection plane S, or by setting the vicinity of the surgical tool as the position of the viewpoint P, it is assumed that possibility of acquiring an image regarding the user's attention target will be increased (Geometric Transformation Processing)

Conventionally, it has been difficult to enlarge and observe the posterior pole while observing the fundus at a wide angle because the images cannot be acquired simultaneously. In contrast, the intraocular image processing system 1 according to the present embodiment can present a wide angle range and an enlarged view of the posterior pole simultaneously by performing image transformation on the integrated image G.

Figure 22:
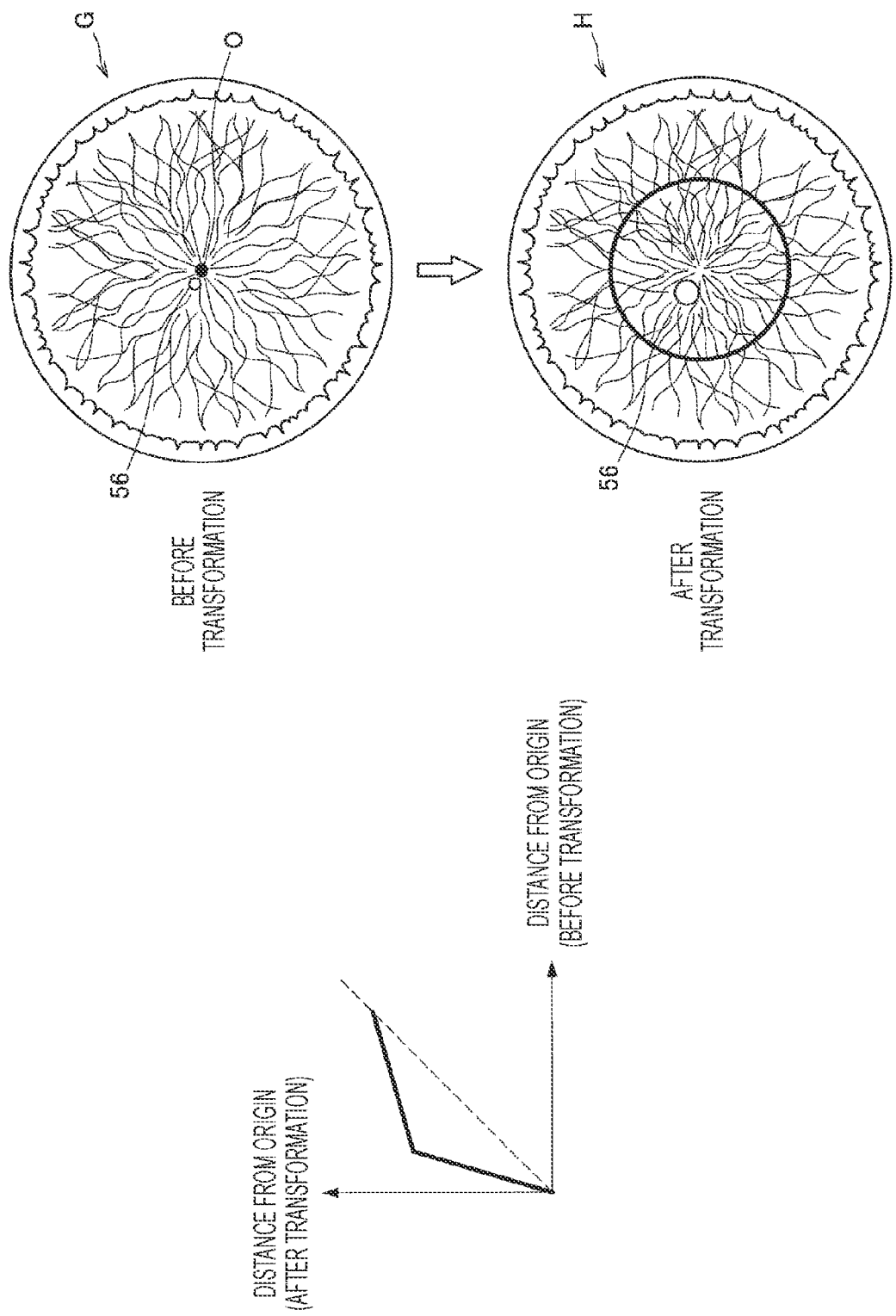
FIG. 22 is an explanatory diagram showing one example of geometric transformation of an integrated image.

FIG. 22 shows one example of geometric transformation of the integrated image G. In such geometric transformation, the integrated image G is transformed by changing a distance on the basis of a function set in advance without changing a direction of a pixel position from a reference point. The function can be set as needed, for example, as shown on the left side of FIG. 22, a function that performs transformation may be used such that a distance ratio before transformation is different from the distance ratio after transformation according to a predetermined distance from the origin. Note that the reference point may be, for example, fixed to the origin O that is the center of the integrated image G, or may be set on the basis of a specified region, for example, the position of the macula or optic disc, the position of the surgical tool, or the like. By transforming the integrated image G by using such a function, the posterior pole 56 near the origin O, which is the reference point, is uniformly enlarged, and the other portions are reduced. As a result, the integrated image G is transformed into an image H that allows good observation of both the entire fundus and the posterior pole.

Furthermore, if a function other than the function shown on the left side of FIG. 22 is used, another geometric transformation is performed on the integrated image G. For example, if the integrated image G is transformed using the function shown in the upper right of FIG. 23, an image Ha having pincushion distortion can be obtained. For example, in a case where the integrated image G before transformation is an image acquired using a wide-angle observation lens and depicts the retina in a planar fashion, such a transformation brings the retina closer to a spherical shape, making it easier to understand intraocular information from the image.

Figure 23:
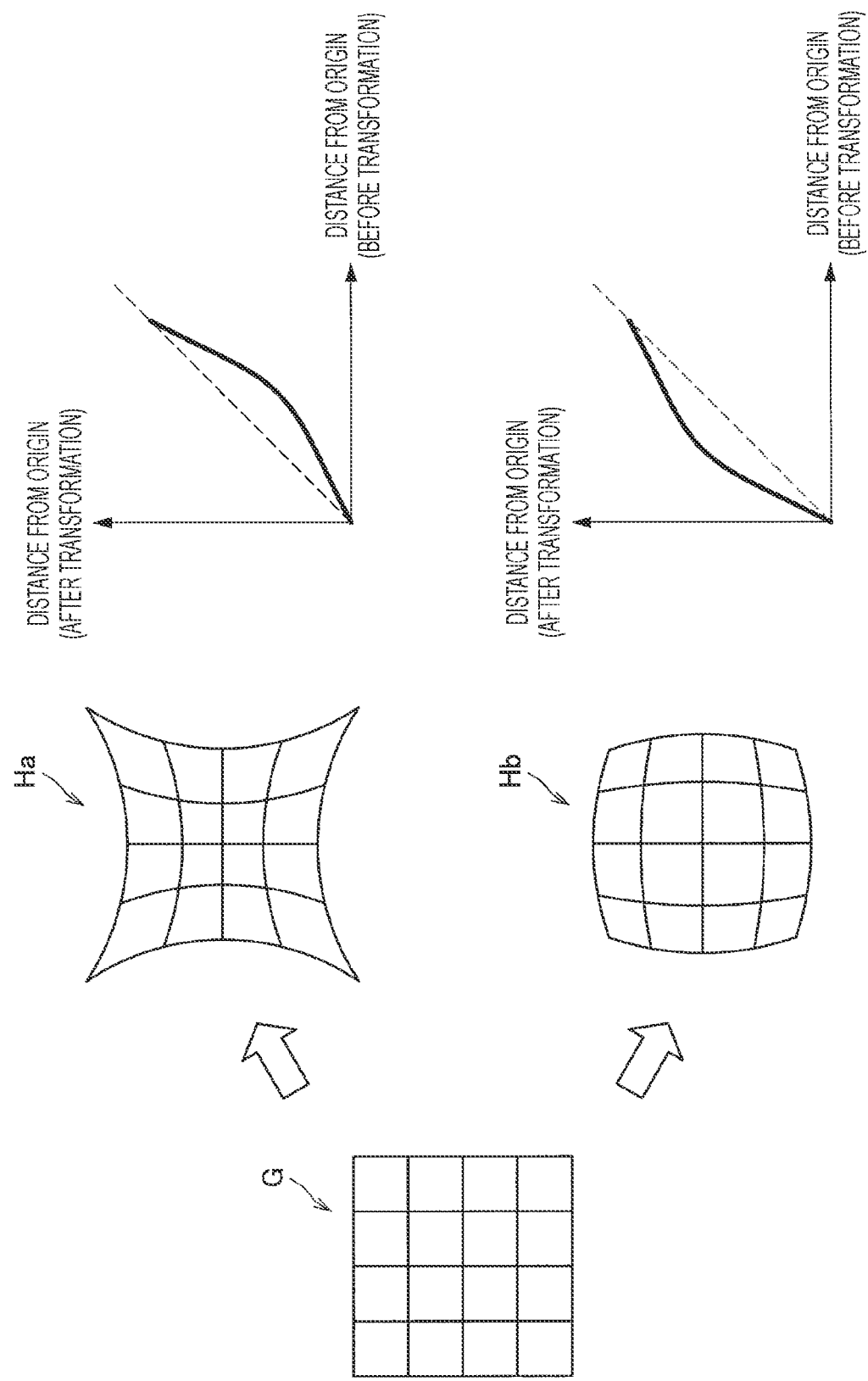
FIG. 23 is an explanatory diagram showing another example of the geometric transformation of the integrated image.
Figure 24:
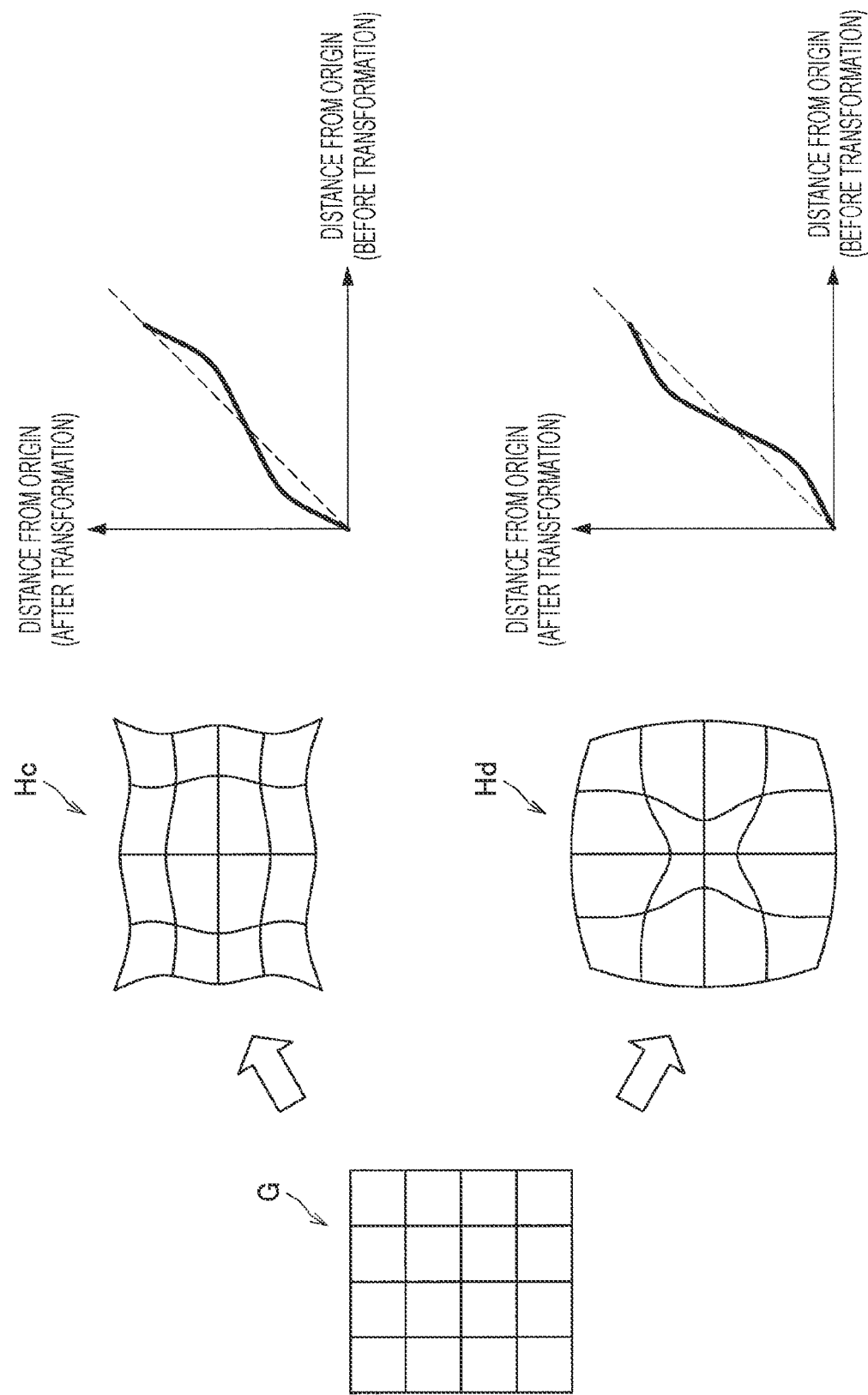
FIG. 24 is an explanatory diagram showing another example of the geometric transformation of the integrated image.

In addition, for example, if the function as shown in the lower right of FIG. 23 is used, the integrated image G can be transformed into an image Hb having barrel distortion. Furthermore, for example, if the function shown in the upper right of FIG. 24 is used, the integrated image G can be transformed into an image Hc having so-called Jingasa type distortion in which both pincushion distortion and barrel distortion appear, with the central portion bulging outward and curves expanding again in the peripheral portion. Moreover, for example, if the function shown in the lower right of FIG. 24 is used, the integrated image G can be transformed into an image Hd having distortion in which both pincushion distortion and barrel distortion appear, with the central portion shrinking inward and the peripheral portion bulging. These functions can be appropriately selected according to preference of the user or the purpose of observation.

(Image Work Indicating Type of Original Image)

The presentation processing unit 140 may work the images g so as to indicate the type of original images g when generating a presentation image H from the integrated image G. As the type of original images, for example, a type according to acquisition time of the images may be shown. That is, the images g are worked to allow distinction between a past image and a current image. As a method of work, for example, the current image may be displayed as it is, and the past image may undergo color transformation by using only grayscale or specified color channel. Furthermore, in a case where the type of original image g is shown according to the type of image generating device 200, for example, the image may be worked by adjusting the luminosity or sharpness of the acquired image g.

Figure 25:
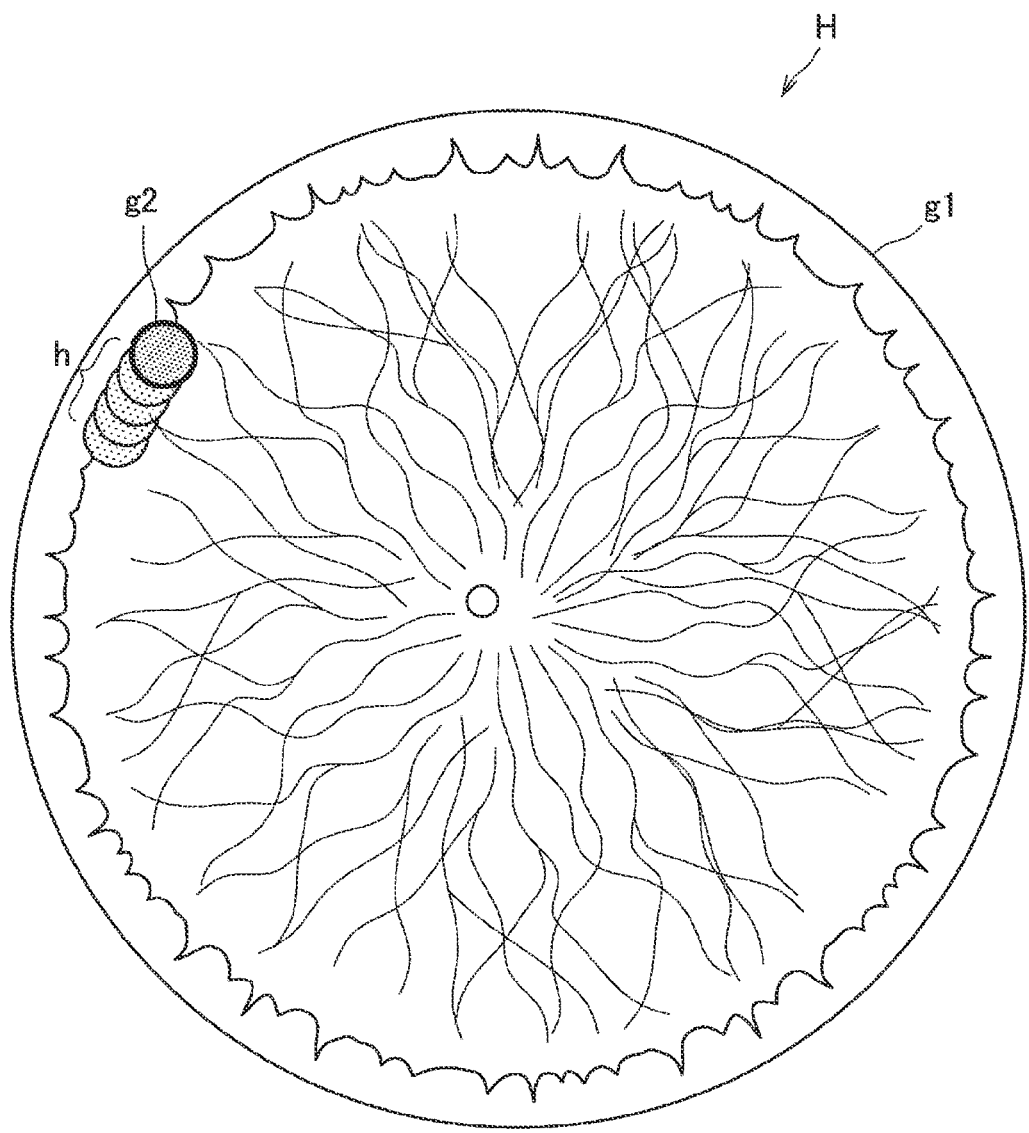
FIG. 25 is an explanatory diagram showing one example of image work based on a type of image.

As one example of the presentation image H, FIG. 25 shows the presentation image H in which for the integrated image of an illustration and an endoscopic image, past images out of the endoscopic image are changed to a grayscale. In the presentation image H shown in FIG. 25, the illustration g1 and the current endoscopic image g2 are images identical to images when integrated. Meanwhile, the past endoscopic images h are images changed to a grayscale by the presentation processing unit 140. In this way, by indicating the type of original image, it becomes possible to present more information with the presentation image H.

(Integrated Image and Single Image Arranged Side by Side)

Depending on details of technique and the type of image generating device 200, it may be more preferable for the user, such as easy to perform technique, to present the image itself generated by the image generating device 200 together with the integrated image than to present only the integrated image generated as described above. In this case, the image generated by the image generating device 200 may be presented together with the integrated image side by side.

Figure 26:
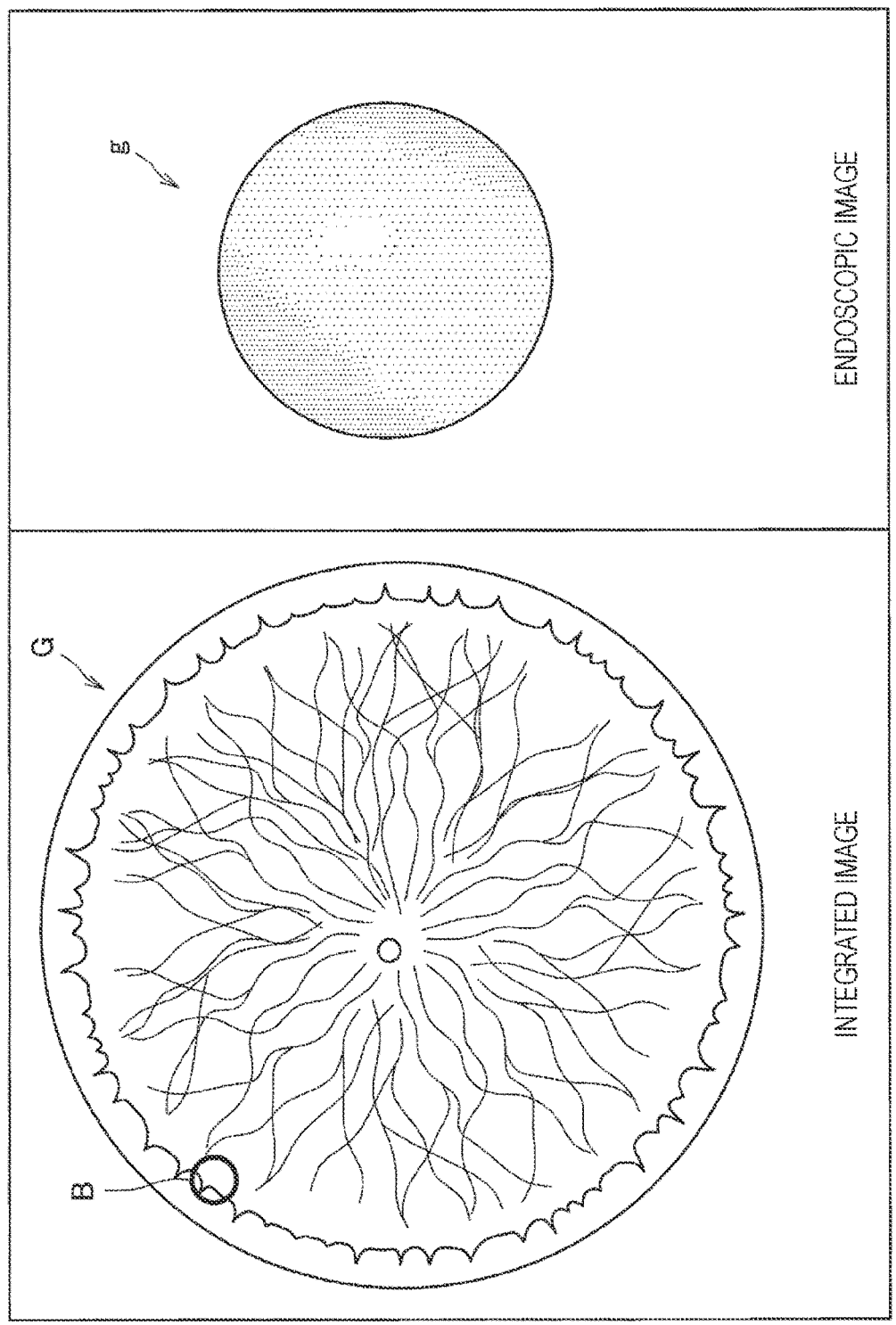
FIG. 26 is an explanatory diagram showing one example of the integrated image and the endoscopic image arranged side by side.
Figure 27:
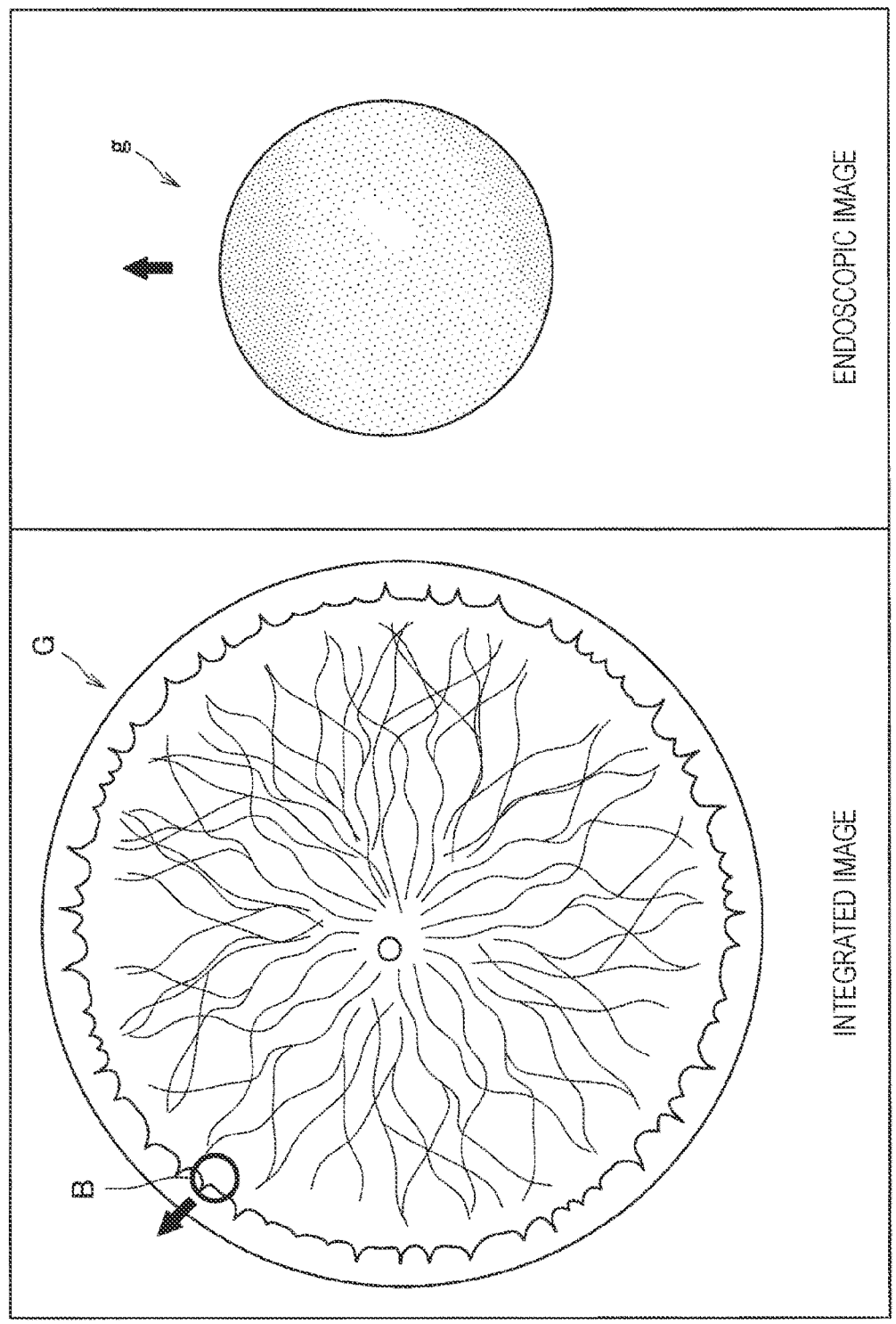
FIG. 27 is an explanatory diagram showing another example of the integrated image and the endoscopic image arranged side by side.

FIGS. 26 and 27 show examples in which the illustration and the endoscopic image captured by the intraocular endoscope are presented side by side. Both FIGS. 26 and 27 show the integrated image G of the illustration and the endoscopic image on the left side, and only the endoscopic image (image g) on the right side. Note that in order to reduce the processing load of generating the integrated image, as the endoscopic image to be integrated with the illustration, a mark indicating the range of the endoscopic image is used instead of the endoscopic image itself. Therefore, the integrated image G is generated by integrating the illustration and the mark indicating the range of the endoscopic image (range B).

When arranging the integrated image and the endoscopic image side by side, for example, as shown in FIG. 26, the presentation direction of the endoscopic image may be aligned with the direction of the image in the integrated image. Alternatively, as shown in FIG. 27, the endoscopic image may be presented such that the upward direction of the endoscopic image is vertically upward, and in the integrated image G, a symbol (for example, an arrow) indicating the direction corresponding to the upward direction of the endoscopic image may be presented together with the range B of the endoscopic image. By arranging the integrated image and the image generated by the image generating device 200 side by side in this manner, the correspondence between the two images can be presented to the user in an easy-to-understand manner. Note that in FIGS. 26 and 27, only one image g is arranged side by side with the integrated image, but the present disclosure is not limited to such an example. A plurality of images g may be presented side by side with the integrated image.

4. HARDWARE CONFIGURATION

Figure 28:
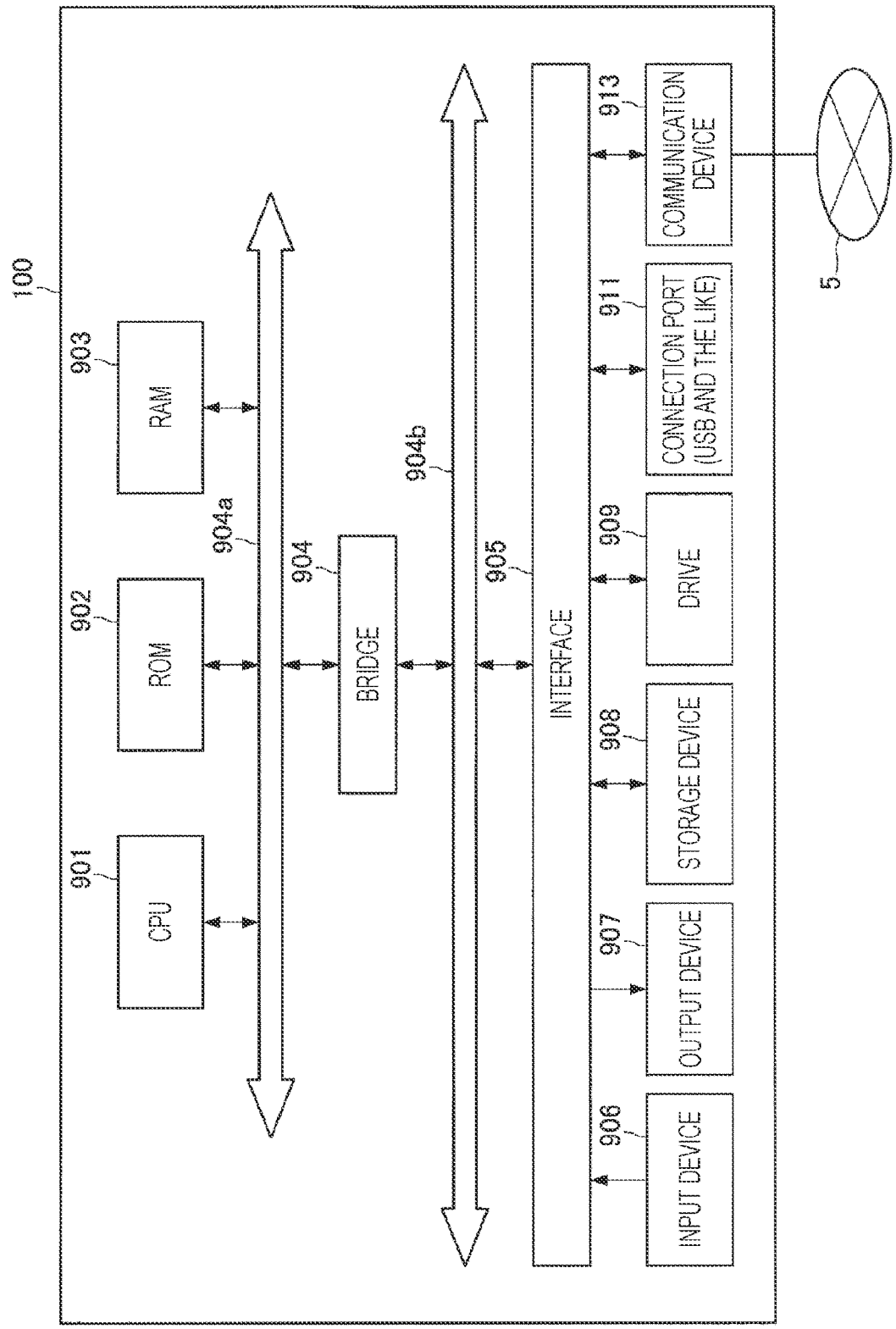
FIG. 28 is a hardware configuration diagram showing a hardware configuration of an image processing device according to the embodiment.

A hardware configuration example of the image processing device 100 of the intraocular image processing system 1 according to the above embodiment will be described. FIG. 28 is a hardware configuration diagram showing the hardware configuration of the image processing device 100 according to the above embodiment.

The image processing device 100 according to the present embodiment can be implemented by a processing device including a computer and the like as described above. As shown in FIG. 28, the image processing device 100 includes a central processing unit (CPU) 901, a read only memory (ROM) 902, a random access memory (RAM) 903, and a host bus 904a. Furthermore, the image processing device 100 includes a bridge 904, an external bus 904b, an interface 905, an input device 906, an output device 907, a storage device 908, a drive 909, a connection port 911, and a communication device 913.

The CPU 901 functions as an arithmetic processing device and a control device, and controls the overall operation in the image processing device 100 in accordance with various programs. Furthermore, the CPU 901 may be a microprocessor. The ROM 902 stores programs, calculation parameters, and the like used by the CPU 901. The RAM 903 temporarily stores programs used in the execution of the CPU 901, parameters that appropriately change in the execution, and the like. These are connected to each other by the host bus 904a including a CPU bus and the like.

The host bus 904a is connected to the external bus 904b such as a peripheral component interconnect/interface (PCI) bus via the bridge 904. Note that the host bus 904a, the bridge 904, and the external bus 904b do not necessarily need to be separated, and these functions may be implemented in one bus.

The input device 906 includes an input unit for the user to input information such as a mouse, a keyboard, a touch panel, a button, a microphone, a switch, and a lever, an input control circuit that generates an input signal on the basis of an input by the user and outputs the input signal to the CPU 901, and the like. The output device 907 includes, for example, a display device such as a liquid crystal display (LCD) device, an organic light emitting diode (OLED) device, and a lamp, and a voice output device such as a speaker.

The storage device 908 is one example of a storage unit of the image processing device 100, and is a device for data storage. The storage device 908 may include a storage medium, a recording device that records data in the storage medium, a reading device that reads data from the storage medium, an erasing device that erases data recorded in the storage medium, and the like. This storage device 908 drives a hard disk and stores programs executed by the CPU 901 or various data.

The drive 909 is a reader-writer for a storage medium, and is built in or externally attached to the image processing device 100. The drive 909 reads information recorded on a mounted removable recording medium such as a magnetic disk, optical disk, magneto-optical disk, semiconductor memory, or the like, and outputs the information to the RAM 903.

The connection port 911 is an interface to be connected to an external device, and is a connection port to an external device capable of transmitting data by, for example, universal serial bus (USB) and the like. Furthermore, the communication device 913 is a communication interface including, for example, a communication device for connecting to a communication network 5 and the like. Furthermore, the communication device 913 may be a wireless local area network (LAN)-compatible communication device, a wireless USB-compatible communication device, or a wire communication device that performs wired communication.

5. CONCLUSION

The configuration of the intraocular image processing system 1 according to the present disclosure and the image processing based on the configuration have been described above. Such an intraocular image processing system 1 integrates images generated by the plurality of image generating devices 200 to generate one integrated image G. The integrated image G shows a wider range than a range of at least an ophthalmologic image acquired by a modality including the surgical microscope, the tomographic acquisition device, the intraocular endoscope, and the like out of respective image generating devices 200. Such an integrated image G makes it possible to simultaneously present wide-range intraocular information that is not obtained with only one modality.

The integrated image G may be a planar image, or can be constructed as a solid model including a sphere model and the like. Generation of the solid integrated image G makes it possible to present a presentation image that allows easy recognition that the retina is spherical.

Furthermore, in the presentation of the integrated image G, for example, by adding work to the integrated image G, information to be presented simultaneously in the integrated image G can be presented to the user to facilitate recognition more easily. For example, it becomes possible to present a wide range of retina and an enlarged portion of the specified portion simultaneously. Furthermore, the geometric transformation of the integrated image G makes it possible to eliminate restrictions due to optical characteristics of the intermediate translucent body to the retina including the optical system of the image generating device 200, and to present an image having a shape that is easy for the user to look at.

Moreover, the presentation method may be changed according to the type of image before being integrated. For example, when presenting a plurality of images acquired by the same image generating device 200 at different times, the images may be worked according to the acquisition time. With this configuration, the use of a past image as the image to be integrated makes it possible to also recognize that the past image is not a current image while extending the range of images to be simultaneously obtained by the integrated image G. Furthermore, the integrated image G and the image itself generated by the image generating device 200 may be presented side by side. For example, for the endoscopic image, the user can more easily understand the endoscopic image in some cases by presenting the endoscopic image with the integrated image G side by side than presenting the endoscopic image in a state of being integrated in the integrated image G. In this way, the integrated image G and the image itself generated by the image generating device 200 may be arranged side by side according to details of technique and the type of image generating device 200.

The preferred embodiment of the present disclosure has been described in detail above with reference to the accompanying drawings, but the technical scope of the present disclosure is not limited to such an example. It is obvious that persons of ordinary skill in the technical field of the present disclosure can conceive various modifications or alterations within the scope of the technical idea described in the claims, and it is of course understood that these also fall within the technical scope of the present disclosure.

Furthermore, effects described in the present specification are merely descriptive or illustrative and not restrictive. That is, the technology according to the present disclosure can produce other effects obvious to those skilled in the art from the description in the present specification, in addition to or instead of the effects described above.

Note that the following configurations also belong to the technical scope of the present disclosure.

(1)

An image processing device including an integration processing unit configured to integrate at least a plurality of intraoperatively acquired images acquired during an ophthalmologic surgical operation by correlating intraocular positions and to generate one integrated image indicating intraocular information in a range wider than an image range of each of the intraoperatively acquired images.

(2)

The image processing device according to (1) described above, in which the intraoperatively acquired images include an image acquired by using a surgical microscope.

(3)

The image processing device according to (1) or (2) described above, in which the intraoperatively acquired images include an image acquired by using a tomographic acquisition device.

(4)

The image processing device according to any one of (1) to (3) described above, in which the intraoperatively acquired images include an image acquired by using an intraocular endoscope.

(5)

The image processing device according to any one of (1) to (4) described above, in which the integration processing unit integrates an illustration regarding a fundus with the intraoperatively acquired images to generate the integrated image.

(6)

The image processing device according to any one of (1) to (5) described above, in which the integrated image is a solid image.

(7)

The image processing device according to any one of (1) to (6) described above, in which the integration processing unit models the integrated image into a substantially spherical shape.

(8)

The image processing device according to any one of (1) to (6) described above, in which the integration processing unit models the integrated image into a solid shape acquired on the basis of the intraoperatively acquired images.

(9)

The image processing device according to any one of (1) to (8) described above, in which the integration processing unit identifies the intraocular positions of the intraoperatively acquired images on the basis of information included in the intraoperatively acquired images and integrates the intraoperatively acquired images.

(10)

The image processing device according to any one of (1) to (9) described above, further including a presentation processing unit configured to process the integrated image according to a presentation format of the integrated image.

(11)

The image processing device according to (10) described above, in which the presentation processing unit transforms the integrated image that is a solid image into a planar image.

(12)

The image processing device according to (10) described above, in which the presentation processing unit performs geometric transformation on the integrated image.

(13)

The image processing device according to any one of (10) to (12) described above, in which the presentation processing unit presents the integrated image to allow identification of types of the intraoperatively acquired images integrated into the integrated image.

(14)

The image processing device according to any one of (10) to (13) described above, in which the presentation processing unit presents the integrated image and at least one of the intraoperatively acquired images arranged side by side.

(15)

An image processing method including: integrating at least a plurality of intraoperatively acquired images acquired during an ophthalmologic surgical operation by correlating intraocular positions; and generating one integrated image indicating intraocular information in a range wider than an image range of each of the intraoperatively acquired images.

(16)

An intraocular image processing system including:

a plurality of image generating devices configured to acquire intraoperatively acquired images during an ophthalmologic surgical operation; and an image processing device configured to integrate at least the plurality of intraoperatively acquired images acquired by the image generating devices by correlating intraocular positions and to generate one integrated image indicating intraocular information in a range wider than an image range of each of the intraoperatively acquired images.

(17)

An image processing device including an integration processing unit configured to integrate ophthalmologic images acquired by a plurality of types of ophthalmologic observation devices by correlating intraocular positions and to generate one integrated image indicating intraocular information in a range wider than a range indicated by each of the ophthalmologic images.

(18)

The image processing device according to (17) described above, in which the ophthalmologic images are images acquired intraoperatively.

(19)

The image processing device according to (17) or (18) described above, in which the ophthalmologic images include an image acquired by using a surgical microscope.

(20)

The image processing device according to any one of (17) to (19) described above, in which the ophthalmologic images include an image acquired by using a tomographic acquisition device.

(21)

The image processing device according to any one of (17) to (20) described above, in which the ophthalmologic images include an image acquired by using an intraocular endoscope.

(22)

The image processing device according to any one of (17) to (21) described above, in which the integration processing unit integrates an illustration regarding a fundus with the ophthalmologic images to generate the integrated image.

(23)

The image processing device according to any one of (17) to (22) described above, in which the integrated image is a solid image.

(24)

The image processing device according to any one of (17) to (22) described above, in which the integration processing unit models the integrated image into a substantially spherical shape.

(25)

The image processing device according to any one of (17) to (24) described above, in which the integration processing unit models the integrated image into a solid shape acquired on the basis of the ophthalmologic images.

(26)

The image processing device according to any one of (17) to (25) described above, in which the integration processing unit identifies intraocular positions of the ophthalmologic images on the basis of information included in the ophthalmologic images and integrates the ophthalmologic images.

(27)

The image processing device according to any one of (17) to (26) described above, further including a presentation processing unit configured to process the integrated image according to a presentation format of the integrated image.

(28)

The image processing device according to (27) described above, in which the presentation processing unit transforms the integrated image that is a solid image into a planar image.

(29)

The image processing device according to (27) described above, in which the presentation processing unit performs geometric transformation on the integrated image.

(30)

The image processing device according to any one of (27) to (29) described above, in which the presentation processing unit presents the integrated image to allow identification of types of the ophthalmologic images integrated into the integrated image.

(31)

The image processing device according to any one of (27) to (30) described above, in which the presentation processing unit presents the integrated image and at least one of the ophthalmologic images arranged side by side.

(32)

An image processing method including: integrating ophthalmologic images acquired by a plurality of types of ophthalmologic observation devices by correlating intraocular positions; and generating one integrated image indicating intraocular information in a range wider than a range indicated by each of the ophthalmologic images.

(33)

An intraocular image processing system including:

a plurality of ophthalmologic observation devices configured to acquire ophthalmologic images during an ophthalmologic surgical operation; and an image processing device configured to integrate a plurality of types of the ophthalmologic images acquired by the ophthalmologic observation devices by correlating intraocular positions and to generate one integrated image indicating intraocular information in a range wider than a range indicated by each of the ophthalmologic images.

REFERENCE SIGNS LIST

1 Intraocular image processing system
10a Contact lens
10b Wide-angle observation lens
20 Intraocular endoscope
21 Grip portion
21a Three-dimensional marker
23 Tip
31 Corneal limbal blood vessel
33 Trocar
35 Corneal limbus
37 Iridocorneal angle
53 Crystalline lens
55 Vitreous body
56 Posterior pole
57 Retina
58 Ora serrata
59 Pars plana
100 Image processing device
110 Interface unit
120 Control unit
130 Integration processing unit
140 Presentation processing unit
200 Image generating device
300 Input device
400 Output device

The invention claimed is:

1. An image processing device, comprising:
an integration processing unit configured to:
identify an intraocular position of each ophthalmologic image of a plurality of ophthalmologic images based on information included in a corresponding ophthalmologic image of the plurality of ophthalmologic images, wherein the plurality of ophthalmologic images is acquired by a plurality of types of ophthalmologic observation devices;
integrate the plurality of ophthalmologic images based on correlation of the intraocular position of each ophthalmologic image of the plurality of ophthalmologic images; and
generate one integrated image that indicates intraocular information in a range wider than a range indicated by each ophthalmologic image of the plurality of ophthalmologic images.

2. The image processing device according to claim 1, wherein the plurality of ophthalmologic images is acquired intraoperatively.

3. The image processing device according to claim 1, wherein the plurality of ophthalmologic images includes an image acquired by a surgical microscope.

4. The image processing device according to claim 1, wherein the plurality of ophthalmologic images includes an image acquired by a tomographic acquisition device.

5. The image processing device according to claim 1, wherein the plurality of ophthalmologic images includes an image acquired by an intraocular endoscope.

6. The image processing device according to claim 1, wherein the integration processing unit is further configured to integrate an illustration regarding a fundus with the plurality of ophthalmologic images to generate the integrated image.

7. The image processing device according to claim 1, wherein the integrated image is a solid image.

8. The image processing device according to claim 1, wherein the integration processing unit is further configured to model the integrated image into a spherical shape.

9. The image processing device according to claim 1, wherein the integration processing unit is further configured to model the integrated image into a solid shape.

10. The image processing device according to claim 1, further comprising a presentation processing unit configured to process the integrated image based on a presentation format of the integrated image.

11. The image processing device according to claim 10, wherein the presentation processing unit is further configured to transform the integrated image that is a solid image into a planar image.

12. The image processing device according to claim 10, wherein the presentation processing unit is further configured to perform geometric transformation on the integrated image.

13. The image processing device according to claim 10, wherein the presentation processing unit is further configured to present the integrated image to allow identification of types of the plurality of ophthalmologic images integrated into the integrated image.

14. The image processing device according to claim 10, wherein the presentation processing unit is further configured to present the integrated image and at least one ophthalmologic image of the plurality of ophthalmologic images side by side.

15. An image processing method, comprising:
identifying an intraocular position of each ophthalmologic image of a plurality of ophthalmologic images based on information included in a corresponding ophthalmologic image of the plurality of ophthalmologic images, wherein the plurality of ophthalmologic images is acquired by a plurality of types of ophthalmologic observation devices;

integrating the plurality of ophthalmologic images based on correlation of the intraocular position of each ophthalmologic image of the plurality of ophthalmologic images; and generating one integrated image indicating intraocular information in a range wider than a range indicated by each ophthalmologic image of the plurality of ophthalmologic images.

16. An intraocular image processing system, comprising:

a plurality of ophthalmologic observation devices configured to acquire a plurality of ophthalmologic images during an ophthalmologic surgical operation; and an image processing device configured to:
- identify an intraocular position of each ophthalmologic image of the plurality of ophthalmologic images based on information included in a corresponding ophthalmologic image of the plurality of ophthalmologic images;
- integrate the plurality of ophthalmologic images based on correlation of the intraocular position of each ophthalmologic image of the plurality of ophthalmologic images; and
- generate one integrated image that indicates intraocular information in a range wider than a range indicated by each ophthalmologic image of the plurality of ophthalmologic images.

* * * * *